United States Patent
Abolfathi et al.

(10) Patent No.: US 7,664,277 B2
(45) Date of Patent: Feb. 16, 2010

(54) BONE CONDUCTION HEARING AID DEVICES AND METHODS

(75) Inventors: Amir Abolfathi, Woodside, CA (US); John Spiridigliozzi, San Mateo, CA (US)

(73) Assignee: Sonitus Medical, Inc., San Mateo, CA (US)

(*) Notice: Subject to any disclaimer, the term of this patent is extended or adjusted under 35 U.S.C. 154(b) by 0 days.

(21) Appl. No.: 11/754,833

(22) Filed: May 29, 2007

(65) Prior Publication Data

US 2007/0291972 A1 Dec. 20, 2007

Related U.S. Application Data

(60) Provisional application No. 60/809,244, filed on May 30, 2006, provisional application No. 60/820,223, filed on Jul. 24, 2006.

(51) Int. Cl.
*H04R 25/00* (2006.01)
(52) U.S. Cl. .......................... 381/151; 381/312; 600/25
(58) Field of Classification Search ................ 381/151, 381/312, 315, 322, 324, 326, 328, 380; 600/25; 607/56, 57
See application file for complete search history.

(56) References Cited

U.S. PATENT DOCUMENTS

| 2,045,404 | A | 6/1936 | Nicholides |
|---|---|---|---|
| 2,161,169 | A | 6/1939 | Jefferis |
| 2,318,872 | A | 5/1943 | Madiera |
| 2,977,425 | A | 3/1961 | Cole |
| 2,995,633 | A | 8/1961 | Puharich et al. |
| 3,156,787 | A | 11/1964 | Puharich et al. |
| 3,170,993 | A | 2/1965 | Puharich et al. |
| 3,267,931 | A | 8/1966 | Puharich et al. |
| 3,325,743 | A | 6/1967 | Blum |
| 3,787,641 | A | 1/1974 | Santori |
| 3,894,196 | A | 7/1975 | Briskey |
| 3,985,977 | A | 10/1976 | Beaty et al. |

(Continued)

FOREIGN PATENT DOCUMENTS

EP 0715838 A2 6/1996

(Continued)

OTHER PUBLICATIONS

Dental Cements—Premarket Notification, U.S. Department of Health and Human Services Food and Drug Administration Center for Devices and Radiological Health, Aug. 18, 1998, pp. 1-10.*

(Continued)

*Primary Examiner*—Vivian Chin
*Assistant Examiner*—Joseph Saunders, Jr.
(74) *Attorney, Agent, or Firm*—Levine Bagade Han LLP

(57) ABSTRACT

Methods and apparatus for transmitting vibrations via an electronic and/or transducer assembly through a tooth or teeth are disclosed herein. The assembly may include a bracket which is adhered or affixed onto the tooth or teeth and an electronics and/or transducer assembly which may be removably coupled to the bracket. The electronic and/or transducer assembly may receive incoming sounds either directly or through a receiver to process and amplify the signals and transmit the processed sounds via a vibrating transducer element coupled to the bracket for transmission into the underlying tooth or other bone structure.

35 Claims, 24 Drawing Sheets

U.S. PATENT DOCUMENTS

| | | | |
|---|---|---|---|
| 4,025,732 A | 5/1977 | Traunmuller | |
| 4,150,262 A | 4/1979 | Ono | |
| 4,498,461 A | 2/1985 | Hakansson | |
| 4,591,668 A | 5/1986 | Iwata | |
| 4,612,915 A | 9/1986 | Hough et al. | |
| 4,642,769 A | 2/1987 | Petrofsky | |
| 4,738,268 A | 4/1988 | Kipnis | |
| 4,817,044 A | 3/1989 | Ogren | |
| 4,832,033 A | 5/1989 | Maher et al. | |
| 4,920,984 A | 5/1990 | Furumichi et al. | |
| 4,982,434 A | 1/1991 | Lenhardt et al. | |
| 5,012,520 A | 4/1991 | Steeger | |
| 5,033,999 A | 7/1991 | Mersky | |
| 5,047,994 A | 9/1991 | Lenhardt et al. | |
| 5,060,526 A | 10/1991 | Barth et al. | |
| 5,082,007 A | 1/1992 | Adell | |
| 5,233,987 A | 8/1993 | Fabian et al. | |
| 5,323,468 A | 6/1994 | Bottesch | |
| 5,325,436 A | 6/1994 | Soli et al. | |
| 5,372,142 A | 12/1994 | Madsen et al. | |
| 5,402,496 A | 3/1995 | Soli et al. | |
| 5,403,262 A | 4/1995 | Gooch | |
| 5,447,489 A * | 9/1995 | Issalene et al. | 600/25 |
| 5,455,842 A | 10/1995 | Merskey et al. | |
| 5,460,593 A * | 10/1995 | Mersky et al. | 600/25 |
| 5,546,459 A | 8/1996 | Sih et al. | |
| 5,558,618 A | 9/1996 | Maniglia | |
| 5,565,759 A | 10/1996 | Dunstan | |
| 5,616,027 A | 4/1997 | Jacobs et al. | |
| 5,624,376 A | 4/1997 | Ball et al. | |
| 5,661,813 A | 8/1997 | Shimauchi et al. | |
| 5,706,251 A | 1/1998 | May | |
| 5,760,692 A | 6/1998 | Block | |
| 5,800,336 A | 9/1998 | Ball et al. | |
| 5,812,496 A | 9/1998 | Peck | |
| 5,828,765 A * | 10/1998 | Gable | 381/386 |
| 5,902,167 A | 5/1999 | Filo et al. | |
| 5,914,701 A | 6/1999 | Gersheneld et al. | |
| 5,961,443 A | 10/1999 | Rastatter et al. | |
| 5,984,681 A | 11/1999 | Huang | |
| 6,029,558 A | 2/2000 | Stevens et al. | |
| 6,047,074 A | 4/2000 | Zoels et al. | |
| 6,068,590 A | 5/2000 | Brisken | |
| 6,072,884 A | 6/2000 | Kates | |
| 6,072,885 A | 6/2000 | Stockham, Jr. et al. | |
| 6,075,557 A | 6/2000 | Holliman et al. | |
| 6,115,477 A | 9/2000 | Filo et al. | |
| 6,118,882 A | 9/2000 | Haynes | |
| 6,171,229 B1 | 1/2001 | Kroll et al. | |
| 6,223,018 B1 | 4/2001 | Fukumoto et al. | |
| 6,239,705 B1 | 5/2001 | Glen | |
| 6,333,269 B2 | 12/2001 | Naito et al. | |
| 6,377,693 B1 | 4/2002 | Lippa et al. | |
| 6,394,969 B1 | 5/2002 | Lenhardt | |
| 6,504,942 B1 | 1/2003 | Hong et al. | |
| 6,538,558 B2 | 3/2003 | Sakazume et al. | |
| 6,585,637 B2 | 7/2003 | Brillhart et al. | |
| 6,631,197 B1 | 10/2003 | Taenzer | |
| 6,633,747 B1 | 10/2003 | Reiss | |
| 6,682,472 B1 | 1/2004 | Davis | |
| 6,754,472 B1 | 6/2004 | Williams et al. | |
| 6,778,674 B1 | 8/2004 | Panasik et al. | |
| 6,826,284 B1 | 11/2004 | Benesty et al. | |
| 6,885,753 B2 | 4/2005 | Bank | |
| 6,917,688 B2 | 7/2005 | Yu et al. | |
| 6,941,952 B1 | 9/2005 | Rush, III | |
| 6,954,668 B1 | 10/2005 | Cuozzo | |
| 6,985,599 B2 | 1/2006 | Asnes | |
| 7,003,099 B1 | 2/2006 | Zhang et al. | |
| 7,033,313 B2 | 4/2006 | Lupin et al. | |
| 7,035,415 B2 | 4/2006 | Belt et al. | |
| 7,074,222 B2 | 7/2006 | Westerkull | |
| 7,076,077 B2 | 7/2006 | Atsumi et al. | |
| 7,099,822 B2 | 8/2006 | Zangi | |
| 7,162,420 B2 | 1/2007 | Zangi et al. | |
| 7,171,003 B1 | 1/2007 | Venkatesh et al. | |
| 7,171,008 B2 | 1/2007 | Elko | |
| 7,174,022 B1 | 2/2007 | Zhang et al. | |
| 7,206,423 B1 | 4/2007 | Feng et al. | |
| 7,246,058 B2 | 7/2007 | Burnett | |
| 7,258,533 B2 | 8/2007 | Tanner et al. | |
| 7,269,266 B2 | 9/2007 | Anjanappa et al. | |
| 7,271,569 B2 | 9/2007 | Oglesbee | |
| 7,310,427 B2 | 12/2007 | Retchin et al. | |
| 7,329,226 B1 | 2/2008 | Ni et al. | |
| 7,331,349 B2 | 2/2008 | Brady et al. | |
| 7,333,624 B2 | 2/2008 | Husung | |
| 7,361,216 B2 | 4/2008 | Kangas et al. | |
| 7,409,070 B2 | 8/2008 | Pitulia | |
| 7,486,798 B2 | 2/2009 | Anjanappa et al. | |
| 7,520,851 B2 | 4/2009 | Davis et al. | |
| 7,522,738 B2 | 4/2009 | Miller, III | |
| 7,522,740 B2 | 4/2009 | Julstrom et al. | |
| 2001/0003788 A1 | 6/2001 | Ball et al. | |
| 2001/0051776 A1 | 12/2001 | Lenhardt | |
| 2002/0026091 A1 | 2/2002 | Leysieffer | |
| 2002/0071581 A1 | 6/2002 | Leysieffer et al. | |
| 2002/0077831 A1 | 6/2002 | Numa | |
| 2002/0122563 A1 | 9/2002 | Schumaier | |
| 2002/0173697 A1 | 11/2002 | Lenhardt | |
| 2003/0059078 A1 | 3/2003 | Downs et al. | |
| 2003/0091200 A1 | 5/2003 | Pompei | |
| 2003/0212319 A1 | 11/2003 | Magill | |
| 2004/0057591 A1* | 3/2004 | Beck et al. | 381/315 |
| 2004/0131200 A1 | 7/2004 | Davis | |
| 2004/0141624 A1 | 7/2004 | Davis et al. | |
| 2004/0202339 A1 | 10/2004 | O'Brien, Jr. et al. | |
| 2004/0202344 A1 | 10/2004 | Anjanappa et al. | |
| 2004/0243481 A1 | 12/2004 | Bradbury et al. | |
| 2004/0247143 A1 | 12/2004 | Lantrua et al. | |
| 2005/0037312 A1 | 2/2005 | Uchida | |
| 2005/0067816 A1 | 3/2005 | Buckman | |
| 2005/0070782 A1 | 3/2005 | Brodkin | |
| 2005/0129257 A1 | 6/2005 | Tamura | |
| 2005/0196008 A1 | 9/2005 | Anjanappa et al. | |
| 2005/0241646 A1 | 11/2005 | Sotos et al. | |
| 2006/0008106 A1* | 1/2006 | Harper | 381/374 |
| 2006/0025648 A1 | 2/2006 | Lupin et al. | |
| 2006/0064037 A1 | 3/2006 | Shalon et al. | |
| 2006/0167335 A1 | 7/2006 | Park et al. | |
| 2006/0270467 A1 | 11/2006 | Song et al. | |
| 2006/0275739 A1 | 12/2006 | Ray | |
| 2007/0010704 A1 | 1/2007 | Pitulia | |
| 2007/0036370 A1 | 2/2007 | Granovetter et al. | |
| 2007/0041595 A1 | 2/2007 | Carazo et al. | |
| 2007/0142072 A1 | 6/2007 | Lassally | |
| 2007/0230713 A1 | 10/2007 | Davis | |
| 2007/0242835 A1 | 10/2007 | Davis | |
| 2007/0265533 A1 | 11/2007 | Tran | |
| 2007/0276270 A1 | 11/2007 | Tran | |
| 2007/0286440 A1 | 12/2007 | Abolfathi et al. | |
| 2008/0019557 A1 | 1/2008 | Bevirt et al. | |
| 2008/0021327 A1 | 1/2008 | El-Bialy et al. | |
| 2008/0064993 A1 | 3/2008 | Abolfathi et al. | |
| 2008/0070181 A1 | 3/2008 | Abolfathi et al. | |
| 2008/0304677 A1 | 12/2008 | Abolfathi et al. | |
| 2009/0028352 A1 | 1/2009 | Petroff | |
| 2009/0052698 A1 | 2/2009 | Rader et al. | |
| 2009/0088598 A1 | 4/2009 | Abolfathi | |
| 2009/0097684 A1 | 4/2009 | Abolfathi et al. | |
| 2009/0097685 A1 | 4/2009 | Menzel et al. | |
| 2009/0099408 A1 | 4/2009 | Abolfathi et al. | |
| 2009/0105523 A1 | 4/2009 | Kassayan et al. | |
| 2009/0147976 A1 | 6/2009 | Abolfathi | |

| | | | |
|---|---|---|---|
| 2009/0149722 | A1 | 6/2009 | Abolfathi et al. |
| 2009/0180652 | A1 | 7/2009 | Davis et al. |

FOREIGN PATENT DOCUMENTS

| | | | |
|---|---|---|---|
| EP | 0741940 A1 | 11/1996 | |
| EP | 0824889 A1 | 2/1998 | |
| EP | 1299052 A1 | 2/2002 | |
| EP | 1633284 A1 | 12/2004 | |
| EP | 1691686 A1 | 8/2006 | |
| EP | 1718255 A1 | 11/2006 | |
| EP | 1783919 A1 | 5/2007 | |
| JP | 2007028248 A2 | 2/2007 | |
| JP | 2007028610 A2 | 2/2007 | |
| JP | 2007044284 A2 | 2/2007 | |
| JP | 2007049599 A2 | 2/2007 | |
| JP | 2007049658 A2 | 2/2007 | |
| WO | WO 83/02047 | 6/1983 | |
| WO | WO 91/02678 | 3/1991 | |
| WO | WO 95/19678 | 7/1995 | |
| WO | WO 96/21335 | 7/1996 | |
| WO | WO 02/09622 | 2/2002 | |
| WO | WO 2004/045242 | 5/2004 | |
| WO | WO 2004/105650 | 12/2004 | |
| WO | WO 2005/000391 | 1/2005 | |
| WO | WO 2005/037153 | 4/2005 | |
| WO | WO 2005/053533 | 6/2005 | |
| WO | WO 2006/088410 | 8/2006 | |
| WO | WO 2006/130909 | 12/2006 | |
| WO | WO 2007/043055 | 4/2007 | |
| WO | WO 2007/059185 | 5/2007 | |
| WO | WO 2007052251 A2 * | 5/2007 | |
| WO | WO 2007/140367 | 12/2007 | |
| WO | WO 2007/140368 | 12/2007 | |
| WO | WO 2007/140373 | 12/2007 | |
| WO | WO 2007/143453 | 12/2007 | |
| WO | WO 2008/024794 | 2/2008 | |
| WO | WO 2008/030725 | 3/2008 | |
| WO | WO 2009/014812 | 1/2009 | |
| WO | WO 2009/025917 | 2/2009 | |
| WO | WO 2009/066296 | 5/2009 | |

OTHER PUBLICATIONS

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org.

Berard, G., "Hearing Equals Behavior" [summary], 1993, http://www.bixby.org/faq/tinnitus/treatment.html.

Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.

Dental Cements—Premarket Notification, U.S. Department of Health and Human Services Food and Drug Administration Center for Devices and Radiological Health, pp. 1-10, Aug. 18, 1998.

Henry, et al. "Comparison of Custom Sounds for Achieving Tinnitus Relief," *J Am Acad Audiol*,15:585•598, 2004.

Jastreboff, Pawel, J., "Phantom auditory perception (tinnitus): mechanisms of generation and perception," *Neuroscience Research*, 221-254, 1990, Elsevier Scientific Publishers Ireland, Ltd.

Robb, "Tinnitus Device Directory Part I," *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9), 2021-2033, Sep. 2007.

Stuart, A., et al. "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

U.S. Appl. No. 11/672,264, filed Feb. 7, 2007 in the name of Abolfathi, Non-Final Rejection mailed Apr. 28, 2009.

U.S. Appl. No. 11/672,264, filed Feb. 7, 2007 in the name of Abolfathi, Non-Final Rejection mailed Aug. 6, 2008.

U.S. Appl. No. 11/672,239, filed Feb. 7, 2007 in the name of Abolfathi, Non-final Office Action mailed Jun. 18, 2009.

U.S. Appl. No. 11/672,239, filed Feb. 7, 2007 in the name of Abolfathi, Non-final Office Action mailed Nov. 13, 2008.

U.S. Appl. No. 11/672,250, filed Feb. 7, 2007 in the name of Abolfathi, Non-final Office Action mailed Apr. 21, 2009.

U.S. Appl. No. 11/672,250, filed Feb. 7, 2007 in the name of Abolfathi, Non-final Office Action mailed Aug. 8, 2008.

U.S. Appl. No. 11/672,271, filed Feb. 7, 2007 in the name of Abolfathi, Final Office Action mailed May 18, 2009.

U.S. Appl. No. 11/672,271, filed Feb. 7, 2007 in the name of Abolfathi, Non-final Office Action mailed Aug. 20, 2008.

U.S. Appl. No. 11/741,648, filed Apr. 27, 2007 in the name of Menzel et al., Final Office Action mailed May 18, 2009.

U.S. Appl. No. 11/741,648, filed Apr. 27, 2007 in the name of Menzel et al., Non-final Office Action mailed Sep. 4, 2008.

U.S. Appl. No. 11/754,823, filed May 29, 2007 in the name of Abolfathi et al., Final Office Action mailed May 12, 2009.

U.S. Appl. No. 11/754,823, filed May 29, 2007 in the name of Abolfathi et al., Non-final Office Action mailed Aug. 14, 2008.

U.S. Appl. No. 11/866,345, filed May 29, 2007 in the name of Abolfathi et al., Final Office Action mailed Apr. 15, 2009.

U.S. Appl. No. 11/866,345, filed May 29, 2007 in the name of Abolfathi et al., Non-final Office Action mailed Mar. 19, 2008.

Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

* cited by examiner

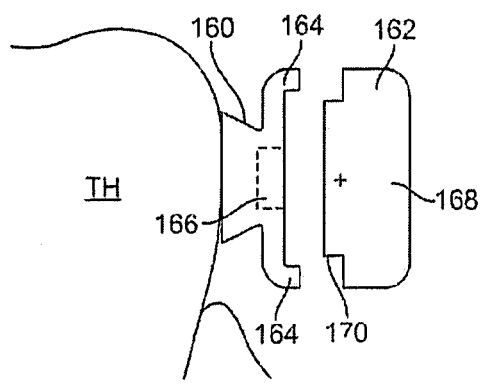 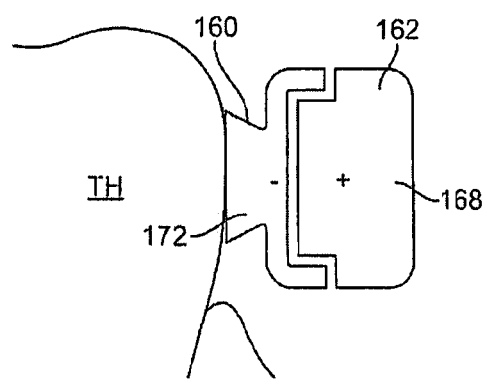
FIG. 16A    FIG. 16B
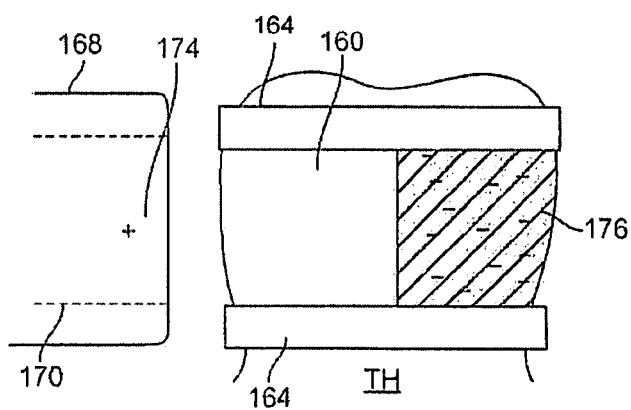
FIG. 16C

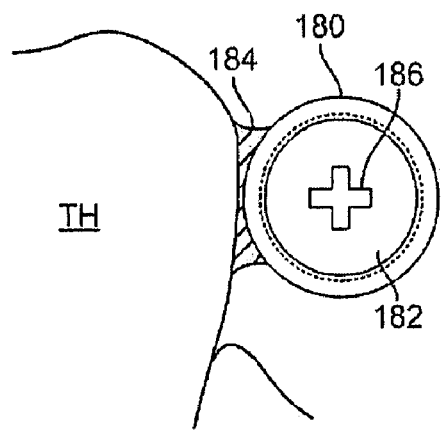
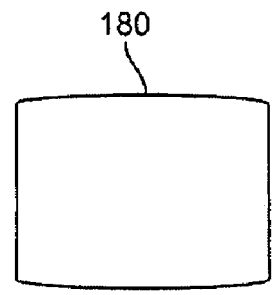
FIG. 17A  FIG. 17B
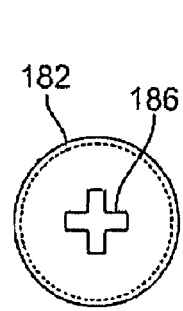
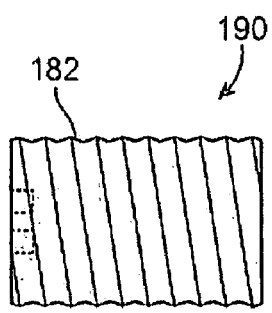
FIG. 17D  FIG. 17C

BONE CONDUCTION HEARING AID DEVICES AND METHODS

CROSS-REFERENCE TO RELATED APPLICATIONS

This application claims the benefit of priority to U.S. Provisional Patent Application Nos. 60/809,244 filed May 30, 2006 and 60/820,223 filed Jul. 24, 2006, each of which is incorporated herein by reference in its entirety.

FIELD OF THE INVENTION

The present invention relates to methods and apparatus for transmitting vibrations through teeth or bone structures in and/or around a mouth. More particularly, the present invention relates to methods and apparatus for sound conduction through teeth or bone structures in and/or around the mouth by transmitting vibrations correlating to auditory signals received by a user.

BACKGROUND OF THE INVENTION

Hearing loss affects over 31 million people in the United States (about 13% of the population). As a chronic condition, the incidence of hearing impairment rivals that of heart disease and, like heart disease, the incidence of hearing impairment increases sharply with age.

While the vast majority of those with hearing loss can be helped by a well-fitted, high quality hearing device, only 22% of the total hearing impaired population own hearing devices. Current products and distribution methods are not able to satisfy or reach over 20 million persons with hearing impairment in the U.S. alone.

Hearing loss adversely affects a person's quality of life and psychological well-being. Individuals with hearing impairment often withdraw from social interactions to avoid frustrations resulting from inability to understand conversations. Recent studies have shown that hearing impairment causes increased stress levels, reduced self-confidence, reduced sociability and reduced effectiveness in the workplace.

The human ear generally comprises three regions: the outer ear, the middle ear, and the inner ear. The outer ear generally comprises the external auricle and the ear canal, which is a tubular pathway through which sound reaches the middle ear. The outer ear is separated from the middle ear by the tympanic membrane (eardrum). The middle ear generally comprises three small bones, known as the ossicles, which form a mechanical conductor from the tympanic membrane to the inner ear. Finally, the inner ear includes the cochlea, which is a fluid-filled structure that contains a large number of delicate sensory hair cells that are connected to the auditory nerve.

Hearing loss can also be classified in terms of being conductive, sensorineural, or a combination of both. Conductive hearing impairment typically results from diseases or disorders that limit the transmission of sound through the middle ear. Most conductive impairments can be treated medically or surgically. Purely conductive hearing loss represents a relatively small portion of the total hearing impaired population (estimated at less than 5% of the total hearing impaired population).

Sensorineural hearing losses occur mostly in the inner ear and account for the vast majority of hearing impairment (estimated at 90-95% of the total hearing impaired population). Sensorineural hearing impairment (sometimes called "nerve loss") is largely caused by damage to the sensory hair cells inside the cochlea. Sensorineural hearing impairment occurs naturally as a result of aging or prolonged exposure to loud music and noise. This type of hearing loss cannot be reversed nor can it be medically or surgically treated; however, the use of properly fitted hearing devices can improve the individual's quality of life.

Conventional hearing devices are the most common devices used to treat mild to severe sensorineural hearing impairment. These are acoustic devices that amplify sound to the tympanic membrane. These devices are individually customizable to the patient's physical and acoustical characteristics over four to six separate visits to an audiologist or hearing instrument specialist. Such devices generally comprise a microphone, amplifier, battery, and speaker. Recently, hearing device manufacturers have increased the sophistication of sound processing, often using digital technology, to provide features such as programmability and multi-band compression. Although these devices have been miniaturized and are less obtrusive, they are still visible and have major acoustic limitation.

Industry research has shown that the primary obstacles for not purchasing a hearing device generally include: a) the stigma associated with wearing a hearing device; b) dissenting attitudes on the part of the medical profession, particularly ENT physicians; c) product value issues related to perceived performance problems; d) general lack of information and education at the consumer and physician level; and e) negative word-of-mouth from dissatisfied users.

Other devices such as cochlear implants have been developed for people who have severe to profound hearing loss and are essentially deaf (approximately 2% of the total hearing impaired population). The electrode of a cochlear implant is inserted into the inner ear in an invasive and non-reversible surgery. The electrode electrically stimulates, the auditory nerve through an electrode array that provides audible cues to the user, which are not usually interpreted by the brain as normal sound. Users generally require intensive and extended counseling and training following surgery to achieve the expected benefit.

Other devices such as electronic middle ear implants generally are surgically placed within the middle ear of the hearing impaired. They are surgically implanted devices with an externally worn component.

The manufacture, fitting and dispensing of hearing devices remain an arcane and inefficient process. Most hearing devices are custom manufactured, fabricated by the manufacturer to fit the ear of each prospective purchaser. An impression of the ear canal is taken by the dispenser (either an audiologist or licensed hearing instrument specialist) and mailed to the manufacturer for interpretation and fabrication of the custom molded rigid plastic casing. Hand-wired electronics and transducers (microphone and speaker) are then placed inside the casing, and the final product is shipped back to the dispensing professional after some period of time, typically one to two weeks.

The time cycle for dispensing a hearing device, from the first diagnostic session to the final fine-tuning session, typically spans a period over several weeks, such as six to eight weeks, and involves multiple with the dispenser.

Accordingly, there exists a need for methods and devices which are efficacious and safe in facilitating the treatment of hearing loss in patients as well as for providing efficient methods for attaching such devices as well as for removing them from the user's mouth without compromising performance.

SUMMARY OF THE INVENTION

An electronic and transducer device may be attached, adhered, or otherwise embedded into or upon a removable dental or oral appliance to form a hearing aid assembly or attached directly to the tooth or upper or lower jaw bone. Such a removable oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

The assembly for transmitting vibrations via at least one tooth may generally comprise, in one variation, a housing having a shape which is conformable to at least a portion of the at least one tooth, and an actuatable transducer disposed within or upon the housing and in vibratory communication with a surface of the at least one tooth. Moreover, the transducer itself may be a separate assembly from the electronics and may be positioned along another surface of the tooth.

In other variations utilizing multiple components, generally a first component may be attached to the tooth or teeth using permanent or semi-permanent adhesives while a second removable component may be attached, adhered, or otherwise affixed to the first component. Examples of adhesives for attaching the first component to the tooth or teeth may include cements and epoxies intended to be applied and/or removed by a healthcare provider. Examples of typical dental cements include, but are not limited to, zinc oxide eugenol, zinc phosphate, zinc silico-phosphate, zinc-polyacrylate, zinc-polycarboxylate, glass ionomer, resin-based, silicate-based cements, etc.

The first component can contain any, all, or none of the mechanisms and/or electronics (e.g., actuators, processors, receivers, etc.) while the second component, which can be attached to the first component, can also contain any combination of the mechanisms and/or electronics, such as the battery. These two components may be temporarily coupled utilizing a variety of mechanisms, e.g., electromagnetic, mechanical attachment, chemical attachment, or a combination of any or all of these coupling mechanisms.

In one example, an electronics and/or transducer assembly may define a channel or groove along a surface for engaging a corresponding dental anchor or bracket which may comprise a light-curable acrylate-based composite material adhered directly to the tooth surface or a metallic bracket (e.g., stainless steel, Nickel-Titanium, Nickel, ceramics, composites, etc.) attached either directly to the tooth or integrated as part of an oral appliance. The dental anchor may be configured in a shape which corresponds to a shape of channel or groove such that the two may be interfitted in a mating engagement. In this manner, the transducer may vibrate directly against the dental anchor which may then transmit these signals directly into the tooth. Sealing the electronics and/or transducer assembly may facilitate the manufacturing of such devices by utilizing a single size for the electronics encasement which may mount onto a custom-fit retainer or bracket.

In yet another variation, a bracket may be ferromagnetic or electromagnetic and removably coupled via magnetic attraction to the housing which may also contain a complementary magnetic component for coupling to the magnetic component. The magnetic portion of the bracket may be confined or the entire bracket may be magnetic. One or more alignment members or arms defined along the bracket may facilitate the alignment of the bracket with the housing by aligning with an alignment step.

Alternative brackets may be configured into a cylindrical configuration sufficiently sized to fit comfortably within the user's mouth. For instance, suitable dimensions for such a bracket may range from 5 to 10 mm in diameter and 10 to 15 mm in length. Alternatively, the bracket may be variously shaped, e.g., ovoid, cubicle, etc. An electronics and/or transducer assembly having an outer surface configured with screw threading may be screwed into the bracket by rotating the assembly into the bracket to achieve a secure attachment for vibrational coupling.

Other variations utilizing a bracket may define a receiving channel into which the electronics and/or transducer assembly may be positioned and secured via a retaining tab. Yet other variations may utilize a protruding stop member for securing the two components to one another or other mechanical mechanisms for coupling.

Aside from mechanical coupling mechanisms, chemical attachment may also be utilized. The electronics and/or transducer assembly may be adhered to the bracket via a non-permanent adhesive, e.g., eugenol and non-eugenol cements. Examples of eugenol temporary cements include, but are not limited to, zinc oxide eugenol commercially available from Temrex (Freeport, N.Y.) or TempoCem® available from Zenith Dental (Englewood, N.J.). Other examples of non-eugenol temporary cements include, but are not limited to, cements which are commercially available such as PROVIS-CELL™ (Septodont, Inc., Ontario, Canada) as well as NOMIX™ (Centrix, Inc., Shelton, Conn.).

BRIEF DESCRIPTION OF THE DRAWINGS

FIG. 16A shows an end view of a bracket containing a magnetic component for removably coupling via magnetic attraction to a housing also containing a complementary magnetic component.

FIG. 16B shows an end view of another variation where the entire bracket is magnetic for magnetically coupling to the housing.

FIG. 16C shows a top view of yet another variation where a magnetic component may be disposed at a first end of the housing and a complementary magnetic component may be disposed at a first end of the bracket.

FIGS. 17A and 17B show end and side views, respectively, of a bracket having a cylindrical configuration.

FIGS. 17C and 17D show assembly side and end views, respectively, of an electronics and/or transducer assembly having a threaded outer surface configured to be screwed into a threaded housing opening of the bracket.

DETAILED DESCRIPTION OF THE INVENTION

An electronic and transducer device may be attached, adhered, or otherwise embedded into or upon a removable oral appliance or other oral device to form a hearing aid assembly. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1:
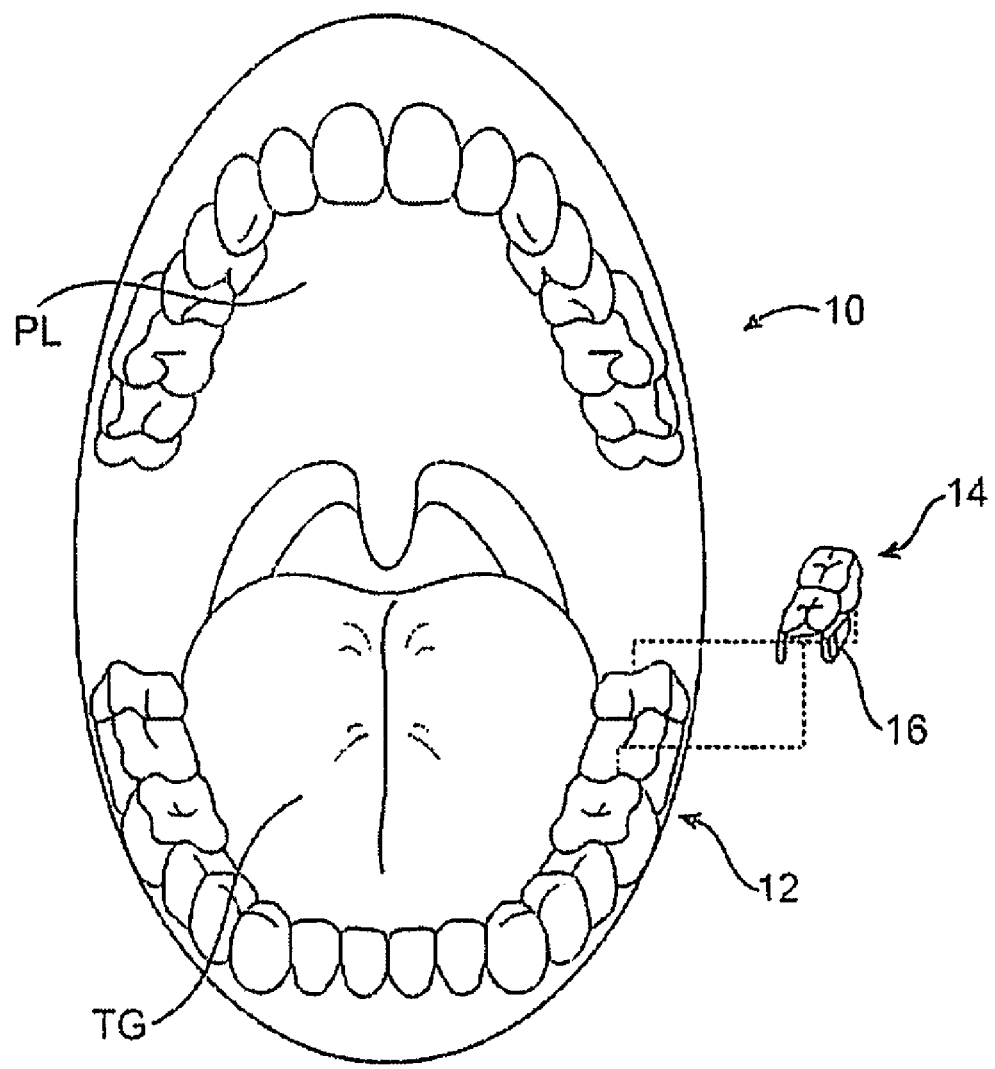
FIG. 1 illustrates the dentition of a patient's teeth and one variation of a hearing aid device which is removably placed upon or against the patient's tooth or teeth as a removable oral appliance.

As shown in FIG. 1, a patient's mouth and dentition 10 is illustrated showing one possible location for removably attaching hearing aid assembly 14 upon or against at least one tooth, such as a molar 12. The patient's tongue TG and palate PL are also illustrated for reference. An electronics and/or transducer assembly 16 may be attached, adhered, or otherwise embedded into or upon the assembly 14, as described below in further detail.

Figure 2:
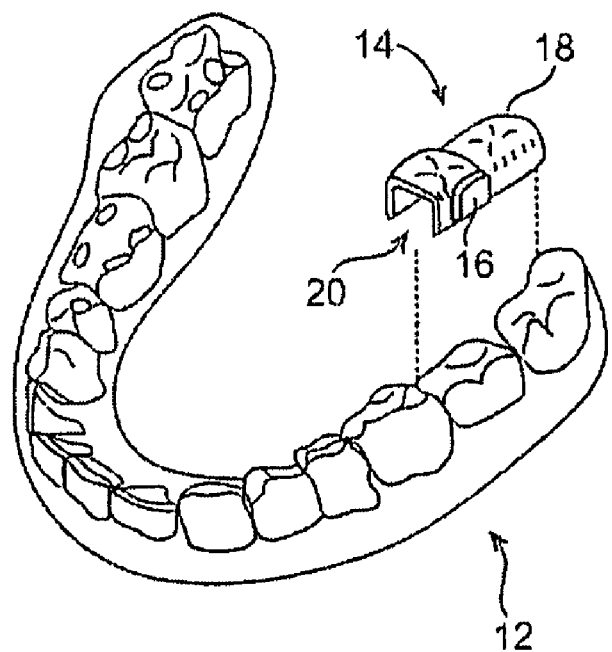
FIG. 2 illustrates a perspective view of the lower teeth showing one exemplary location for placement of the removable oral appliance hearing aid device.
Figure 3:
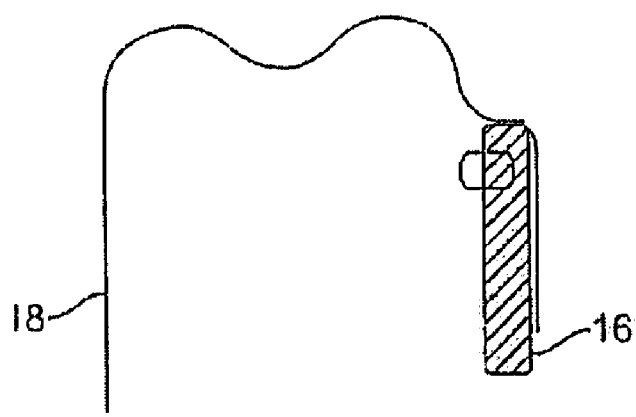
FIG. 3 illustrates a partial cross-sectional view of the hearing aid where the electronics and/or transducer assembly may be embedded into the removable custom-made oral appliance.

FIG. 2 shows a perspective view of the patient's lower dentition illustrating the hearing aid assembly 14 comprising a removable oral appliance 18 and the electronics and/or transducer assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or transducer assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein. In one variation, a partial cross-sectional view of the hearing aid assembly 14 is shown in FIG. 3 where the electronics and/or transducer assembly 16 may be embedded into the removable custom-made oral appliance 18.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g., stereolithography apparatus (SLA), selective laser sintering (SLS), and/or other similar processes utilizing three-dimensional geometry of the patient's dentition, which may be obtained via any number of techniques. Such techniques may include use of scanned dentition using intraoral scanners such as laser, white light, ultrasound, mechanical three-dimensional touch scanners, magnetic resonance imaging (MRI), computed tomography (CT), other optical methods, etc.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the transducer assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth as the appliance 18 may have a resulting size slightly smaller than the scanned tooth or teeth upon which the appliance 18 was formed. The fitting may result in a secure interference fit between the appliance 18 and underlying dentition.

Figure 4:
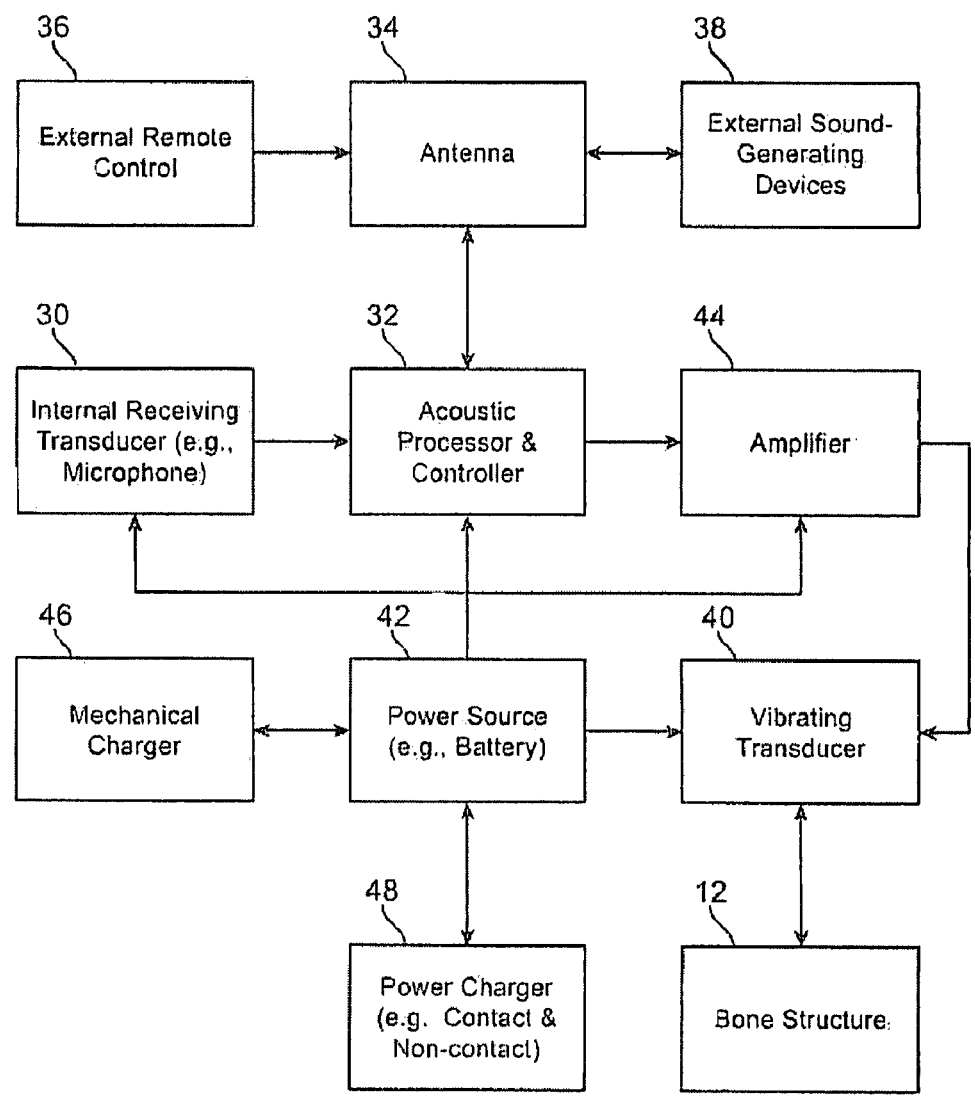
FIG. 4 illustrates a schematic representation of one variation of the hearing aid assembly utilizing a receiving transducer which may generally comprise at least one microphone for receiving sounds and which is electrically connected to a processor for processing the auditory signals.

FIG. 4 illustrates a schematic representation of one variation of hearing aid assembly 14 utilizing receiving transducer 30, which may generally comprise microphone for receiving sounds and which is electrically connected to processor 32 for processing the auditory signals. Processor 32 may be electrically connected to antenna 34 for receiving wireless communication signals, e.g., input control signals from an external remote control 36 and/or other external sound generating devices, e.g., cell phones, telephones, stereos, MP3 players, and other media players. The microphone 30 and processor 32 may be configured to detect and process auditory signals in any practicable range, but may be configured in one variation to detect auditory signals ranging from, e.g., 250 Hertz to 20,000 Hertz. The detected and processed signals may be amplified via amplifier 44, which increases the output levels for vibrational transmission by transducer 40 into the adjacent, or otherwise coupled, bone structure such as a patient's tooth or teeth 12.

With respect to microphone 30, a variety of various microphone systems may be utilized. For instance, microphone 30 may be a digital, analog, piezo, and/or directional type microphone. Such various types of microphones may be interchangeably configured to be utilized with the assembly, if so desired.

Power supply 42 may be connected to each of the components such as processor 32 and transducer 40 to provide power thereto. The control or other sound generated signals received by antenna 34 may be in any wireless form utilizing, e.g., radio frequency, ultrasound, microwave, Blue Tooth® (BLUETOOTH SIG, INC., Bellevue, Wash.), etc. for transmission to assembly 16. The external remote control 36 may be utilized such that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted may be received by electronics and/or transducer assembly 16 via a receiver, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 20,000 Hz.

Although power supply 42 may be a simple battery, replaceable or permanent, other variations may include a power supply 42 which is charged by inductance via an external charger. Additionally, power supply 42 may alternatively be charged via direct coupling 48 to an alternating current (AC) or direct current (DC) source. Other variations may include a power supply 42 which is charged via a mechanical mechanism 46, such as an internal pendulum or slidable electrical inductance charger as known in the art, which is actuated via, e.g., motions of the jaw and/or movement for translating the mechanical motion into stored electrical energy for charging power supply 42.

Figure 5:
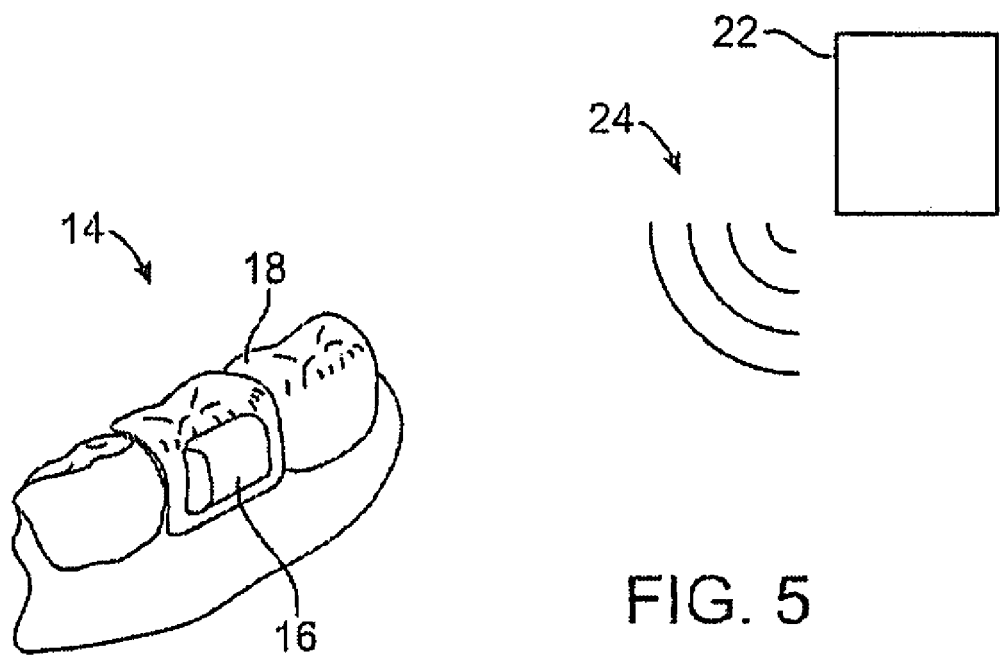
FIG. 5 illustrates an extra-buccal transmitter assembly located outside the patient's mouth to receive auditory signals for processing and transmitting via a wireless signal to the electronics and/or transducer assembly positioned within the patient's mouth.

In one variation, with assembly 14 positioned upon the teeth, as shown in FIG. 5, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 6:
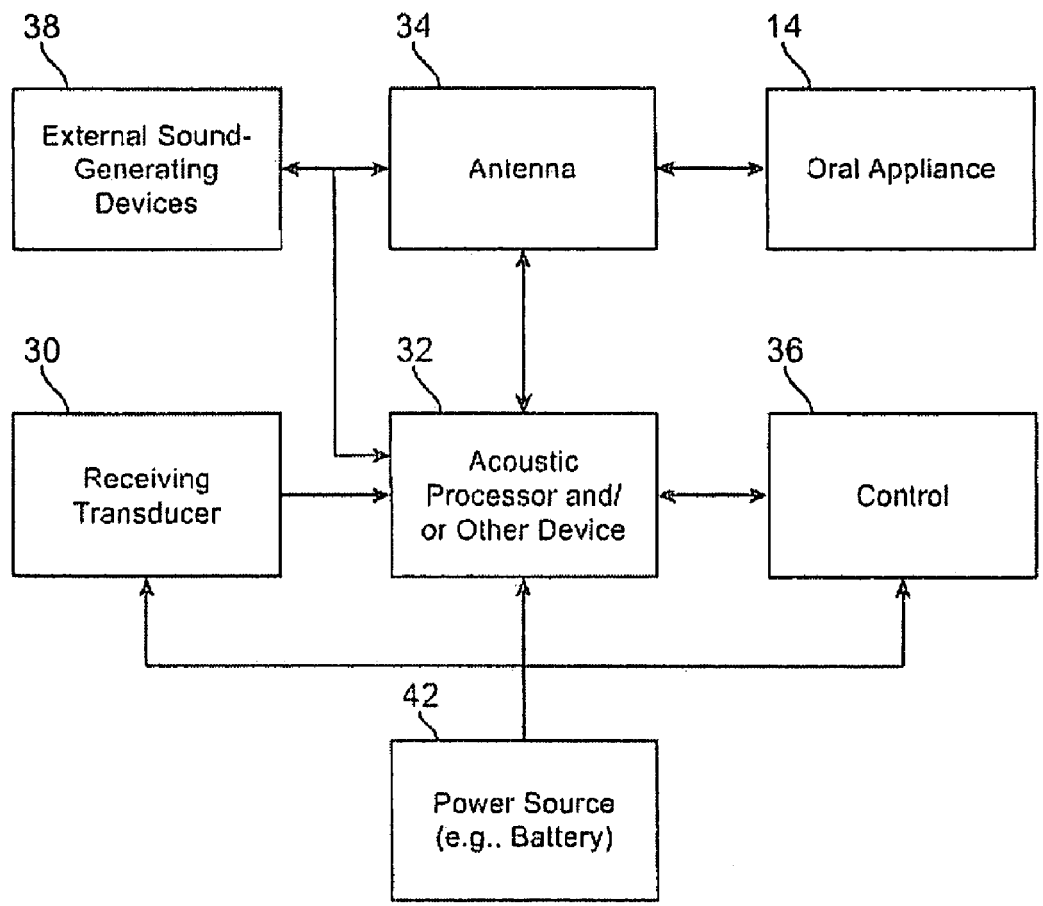
FIG. 6 illustrates a schematic representation of the processor receiving signals via the antenna from external sound-generating devices and controls for modifying various parameters.

In such a variation, as illustrated schematically in FIG. 6, the processor 32 may receive the signals through antenna 34 from external sound-generating devices 38 (as described above, e.g., cell phones, telephones, stereos, MP3 players, and other media players) as well as from other incoming sounds received from receiving transducer 30 for processing and transmission to the hearing aid assembly 14. Control 36 may be used to modify various parameters of the received sound while powered by battery 42, as above.

Figure 7:
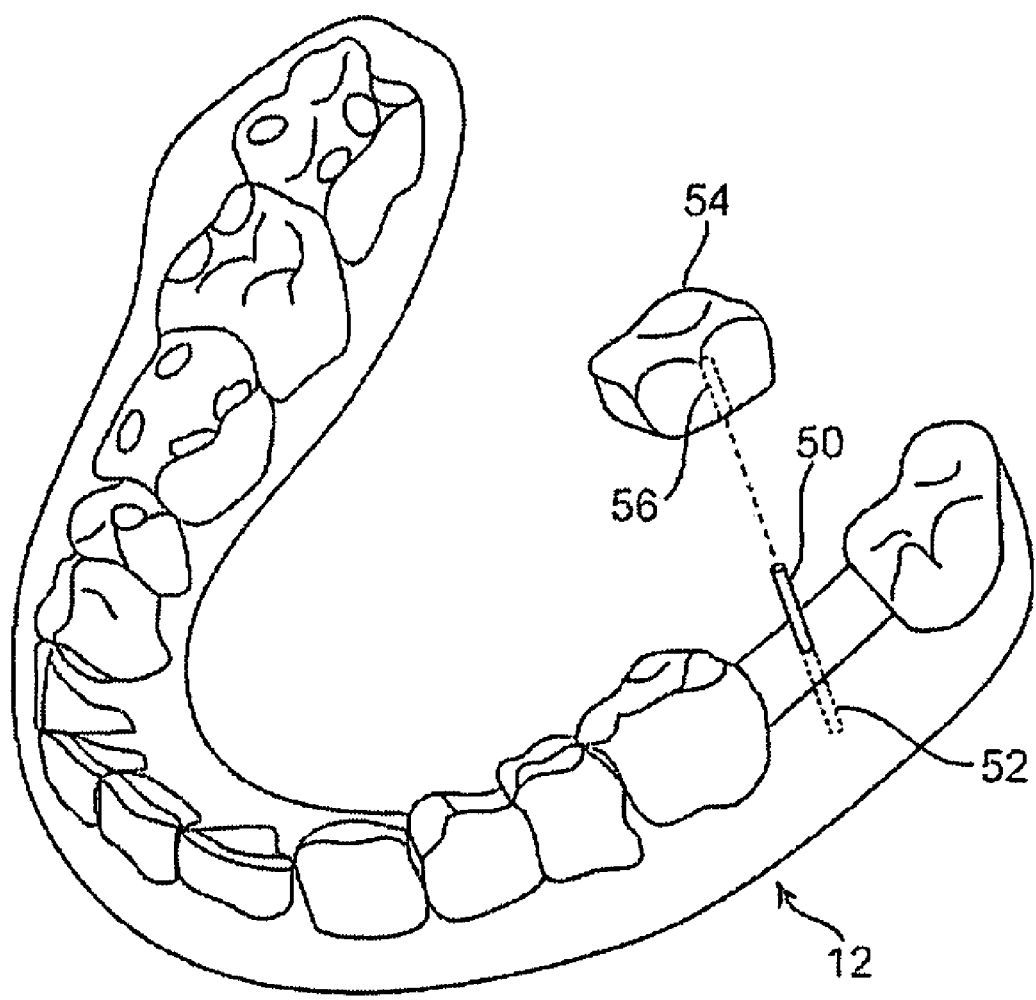
FIG. 7 shows a hearing aid assembly embedded into or configured as a custom made dental implant, e.g., a permanent crown, that may be secured onto an implant post previously implanted into the bone.

In another variation, a hearing aid assembly may be embedded into or configured as a custom made dental implant 54 (e.g., a permanent crown) that may be secured onto an implant post 50 previously implanted into the bone 52, e.g., jaw bone, of a patient, as shown in FIG. 7. Dental implant 54 may be secured or coupled to post 50 via receiving channel 56 defined within implant 54. The transducer assembly as well as the associated electronics and power supply may be contained within implant 54 such that when implant 54 received a signal for conductance to the user, the transducer may vibrate within implant 54 to conduct the vibrations through post 50 and into the user.

Figure 8:
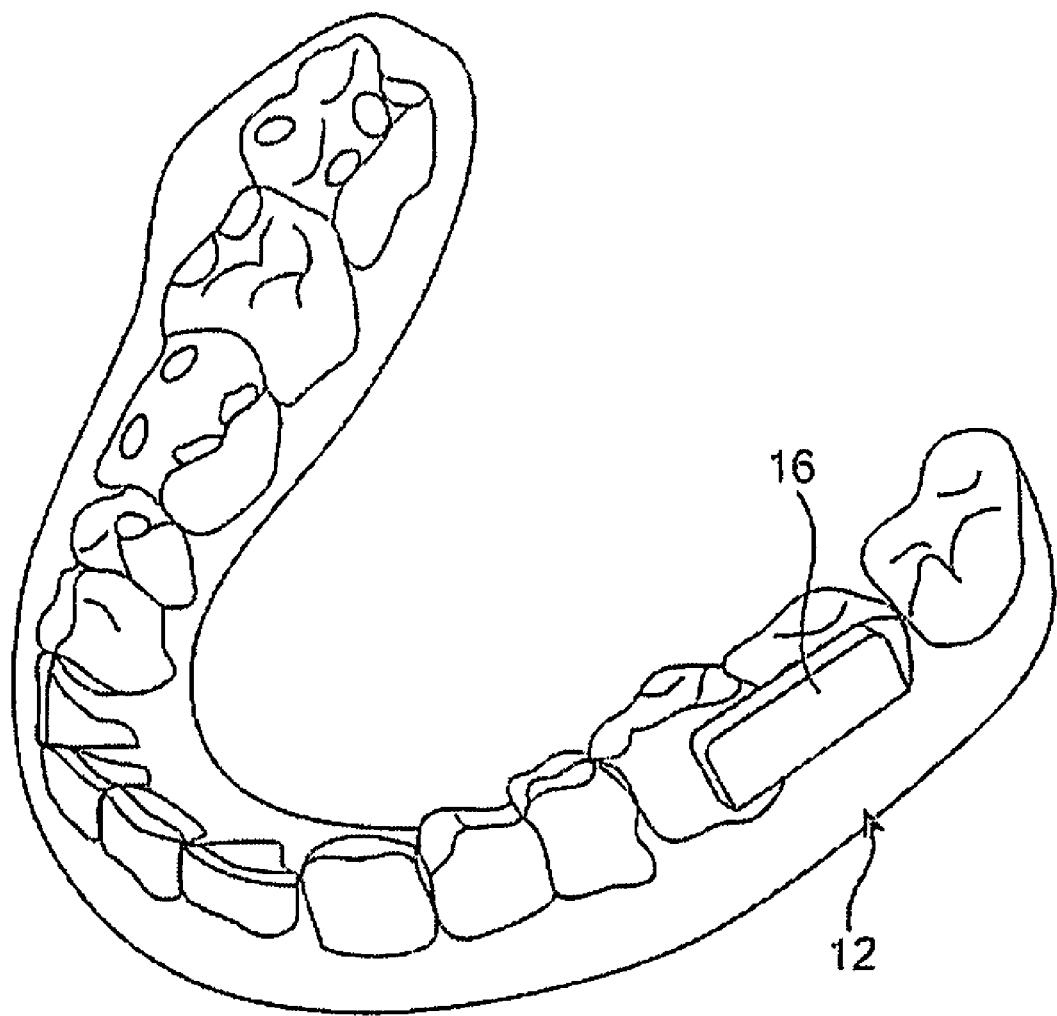
FIG. 8 shows the electronics and transducer assembly bonded or otherwise adhered directly to the surface of one or more teeth rather than being embedded or attached to a separate housing.

In yet another variation, the electronics and transducer assembly 16 may be bonded or otherwise adhered directly to the surface of one or more teeth 12 rather than embedded or attached to a separate housing, as shown in FIG. 8.

Figure 9A:
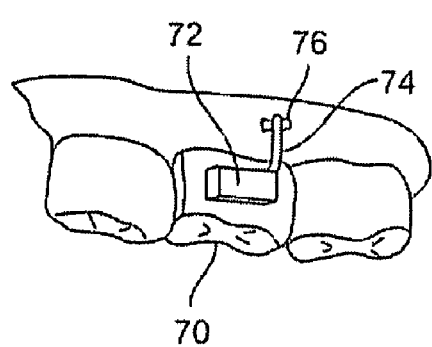
FIGS. 9A and 9B illustrate perspective and side views, respectively, of an oral appliance which may be coupled to a screw or post implanted directly into the underlying bone, such as the maxillary or mandibular bone.
Figure 9B:
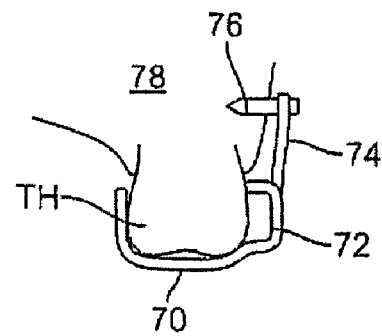

In yet other variations, vibrations may be transmitted directly into the underlying bone or tissue structures rather than transmitting directly through the tooth or teeth of the user. As shown in FIG. 9A, an oral appliance 70 is illustrated positioned upon the user's tooth, in this example upon a molar located along the upper row of teeth. The electronics and/or transducer assembly 72 is shown as being located along the buccal surface of the tooth. Rather than utilizing a transducer in contact with the tooth surface, a conduction transmission member 74, such as a rigid or solid metallic member, may be coupled to the transducer in assembly 72 and extend from oral appliance 70 to a post or screw 76 which is implanted directly into the underlying bone 78, such as the maxillary bone, as shown in the partial cross-sectional view of FIG. 9B. As the distal end of transmission member 74 is coupled directly to post or screw 76, the vibrations generated by the transducer may be transmitted through transmission member 74 and directly into post or screw 76, which in turn transmits the vibrations directly into and through the bone 78 for transmission to the user's inner ear.

Figure 10:
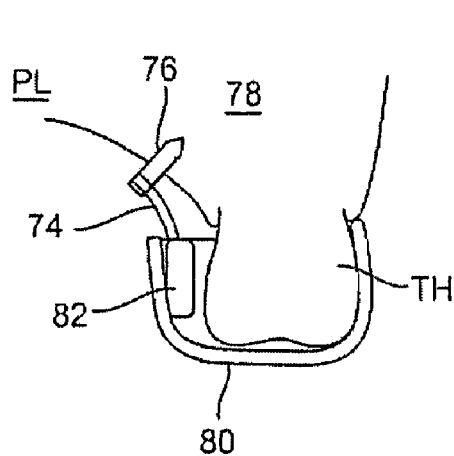
FIG. 10 illustrates another variation in which the oral appliance may be coupled to a screw or post implanted directly into the palate of a patient.
Figure 11:
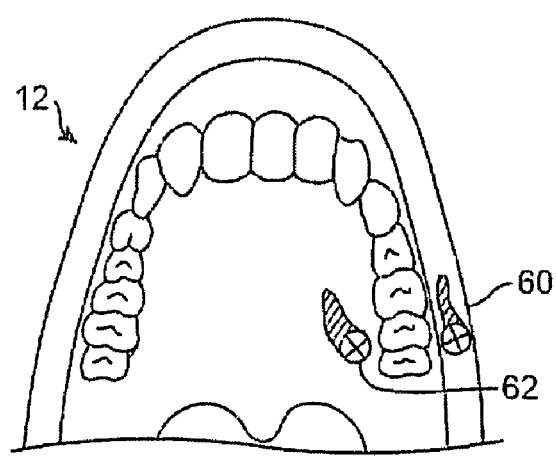
FIG. 11 illustrates several screws drilled into several locations within the user's mouth.

FIG. 10 illustrates a partial cross-sectional view of an oral appliance 80 placed upon the user's tooth TH with the electronics and/or transducer assembly 82 located along the lingual surface of the tooth. Similarly, the vibrations may be transmitted through the conduction transmission member 74 and directly into post or screw 76, which in this example is implanted into the palatine bone PL. Other variations may utilize this arrangement located along the lower row of teeth for transmission to a post or screw 76 drilled into the mandibular bone. In yet other variations, one or more screws may be drilled into several locations within the user's mouth. For instance, two screws 60, 62 may be drilled along the maxillary and palatine bone, as shown in FIG. 11.

Additional examples of various transducer configurations and elements which may be utilized with any of the configurations described herein, as practicable, are shown and described in further detail in U.S. patent application Ser. No. 11/741,648 filed Apr. 27, 2007, which is incorporated herein by reference in its entirety.

In other variations utilizing multiple components, generally a first component may be attached to the tooth or teeth using permanent or semi-permanent adhesives while a second removable component may be attached, adhered, or otherwise affixed to the first component. Examples of adhesives for attaching the first component to the tooth or teeth may include cements and epoxies intended to be applied and/or removed by a healthcare provider. Examples of typical dental cements include, but are not limited to, zinc oxide eugenol, zinc phosphate, zinc silico-phosphate, zinc-polyacrylate, zinc-polycarboxylate, glass ionomer, resin-based, silicate-based cements, etc.

The first component can contain any, all, or none of the mechanisms and/or electronics (e.g., actuators, processors, receivers, etc.) while the second component, which can be attached to the first component, can also contain any combination of the mechanisms and/or electronics, such as the battery. These two components may be temporarily coupled utilizing a variety of mechanisms, e.g., electromagnetic, mechanical attachment, chemical attachment, or a combination of any or all of these coupling mechanisms.

Figure 12:
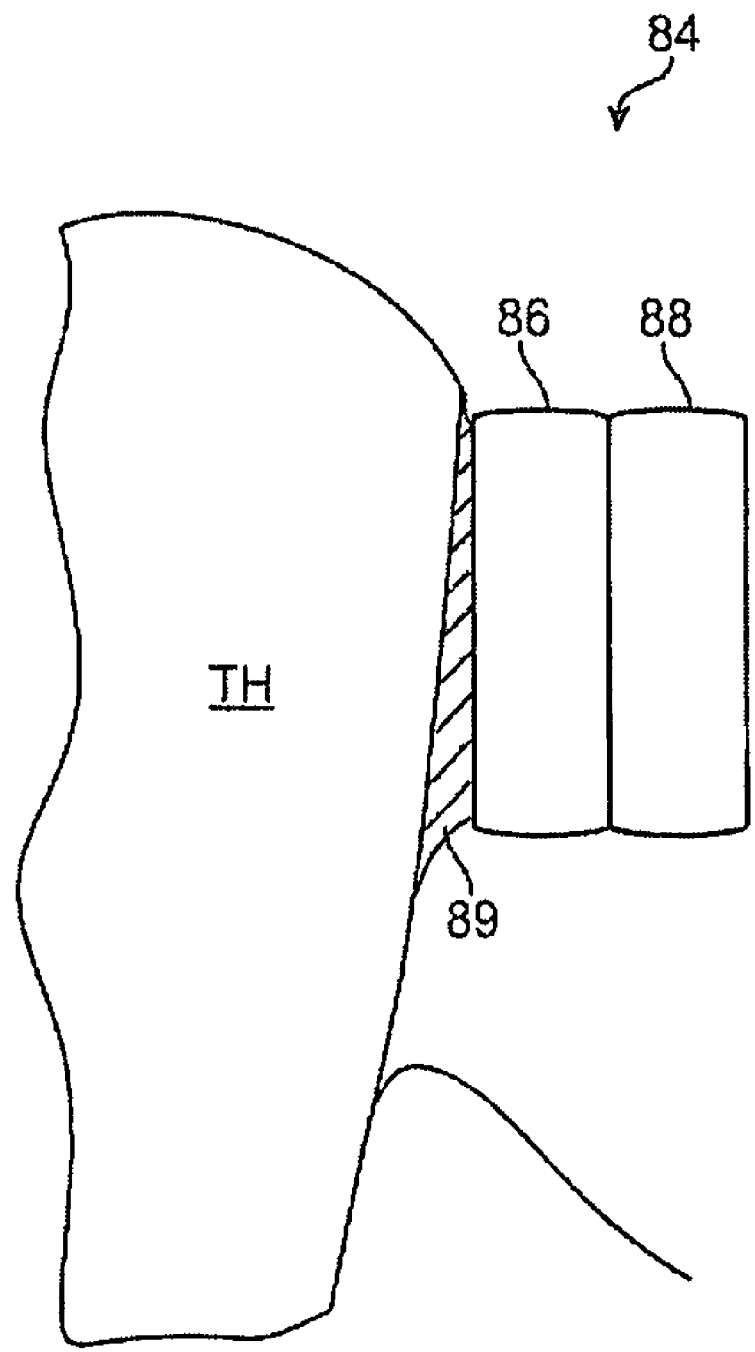
FIG. 12 shows two components of a partially-removable assembly which are configured to securely mate with one another.

An illustrative example is shown in FIG. 12, which shows two components of assembly 84 which are configured to securely mate with one another. A first component 86 may be permanently or non-removably attached onto the underlying tooth or teeth TH and a second component 88 may be removably coupled to the first component 86 by the user. First component 86 may be bonded, adhered, or otherwise affixed via an attachment mechanism 89 such as a cement, epoxy, glue, etc., as mentioned above.

In one variation, the first component 86 may contain a signal processor, transducer, receiver, and any combinations of these components or including additional components. In another variation, the first component may omit each of these elements and function simply as an attachment base for holding and securing the components relative to the tooth. In either case, the second component 88 may comprise a power supply alone, such as a battery, if the remaining components are contained within first component 86 or it may optionally comprise a power supply in combination with a processor, transducer, receiver, etc. Moreover, first and second components 86, 88 may be coupled to one another via any number of magnetic, mechanical, or chemical attachment mechanisms, which are described below in further detail.

Figure 13A:
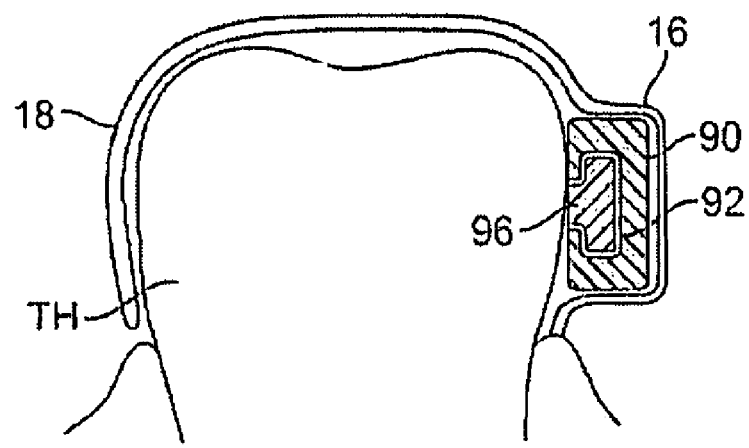
FIG. 13A shows yet another variation of an oral appliance having a composite dental anchor for coupling the transducer to the tooth.

In another variation, an electronics and/or transducer assembly 90 may define a channel or groove 92 along a surface for engaging a corresponding dental anchor or bracket 96, as shown in FIG. 13A. Dental anchor 96 may comprise a light-curable acrylate-based composite material adhered directly to the tooth surface. Moreover dental anchor 96 may be configured in a shape which corresponds to a shape of channel or groove 92 such that the two may be interfitted in a mating engagement. In this manner, the transducer in assembly 90 may vibrate directly against dental anchor 96 which may then transmit these signals directly into the tooth TH. Sealing the electronics and/or transducer assembly 90 may facilitate the manufacturing of such devices by utilizing a single size for the electronics encasement which may mount onto a custom-fit retainer or bracket.

Figure 13B:
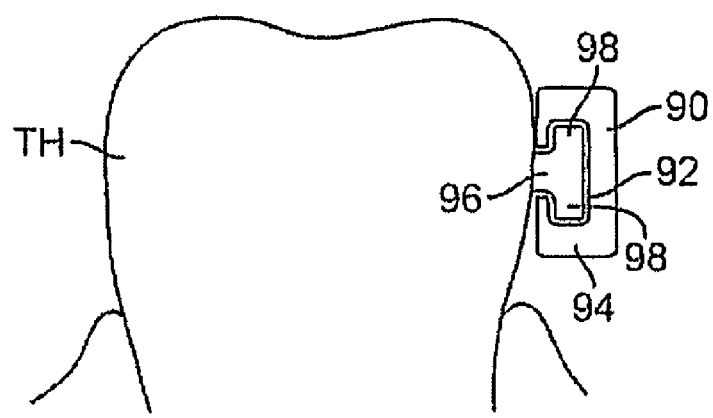
FIG. 13B illustrates a variation in which the oral appliance may be omitted and the electronics and/or transducer assembly may be attached to a composite dental anchor attached directly to the tooth surface.

FIG. 13B shows yet another variation in which the oral appliance is omitted entirely. Here, a composite dental anchor or bracket 96 may be adhered directly onto the tooth surface, as above. Alternatively, bracket 96 may be comprised of a biocompatible material, e.g., stainless steel, Nickel-Titanium, ceramics, composites, etc., formed into a bracket and anchored onto the tooth surface. The bracket 96 may be configured to have a shape 98 over which an electronics and/or transducer assembly 90 may be slid over or upon via a channel 92 having a corresponding receiving configuration 94 for engagement with bracket 96. In this manner, assembly 90 may be directly engaged against bracket 96, through which a transducer may directly vibrate into the underlying tooth TH. Additionally, in the event that assembly 90 is removed from the tooth TH, assembly 90 may be simply slid or rotated off bracket 96 and a replacement assembly may be put in its place upon bracket 96.

Figure 14A:
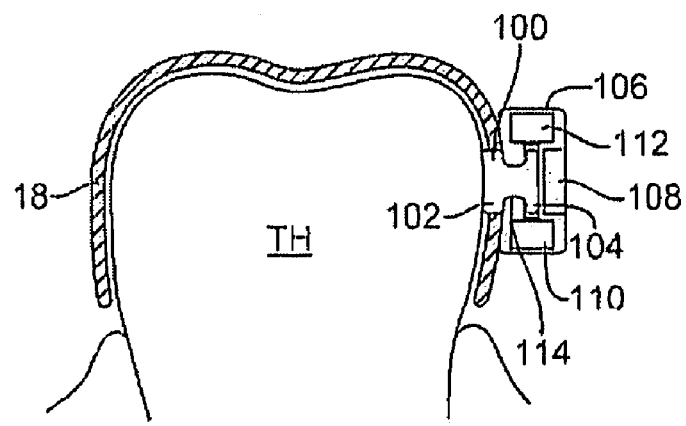
FIG. 14A shows partial cross-sectional end view of yet another variation where a metallic bracket may be integrated directly with or attached directly to an oral appliance such that the metallic bracket directly contacts the tooth.
Figure 14B:
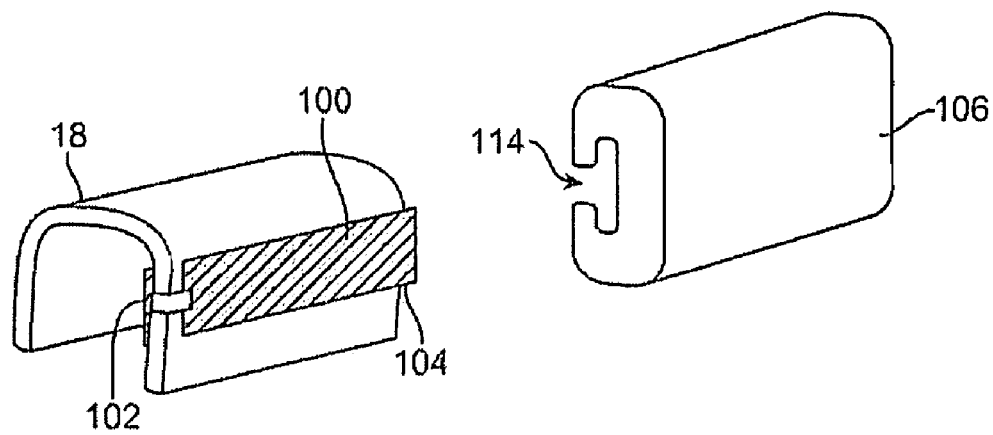
FIG. 14B illustrates a perspective view of the encasement slidingly removed from the metallic bracket.

FIG. 14A shows yet another variation where a metallic bracket 100, fabricated from any of the metals or composites mentioned above, may be integrated directly with or attached directly to oral appliance 18 such that metallic bracket 100 directly contacts tooth TH via an inner contact surface 102 to facilitate coupling and transmission of the vibrations. As also described above, the removable encasement 106 may contain the transducer and many of the electronics, e.g., power supply, receiver, processor, etc., in an enclosure which is hermetically sealed. As above, metallic bracket 100 may have one or more retaining or alignment members 104 which are configured to slidingly or rotatably mate with a complementary retaining channel 114 defined within encasement 106. Also illustrated is an example of positioning of transducer assembly 108, which may contact against metallic bracket 100 when mated, as well as receiver/processor 110 and power supply or battery 112. To remove encasement 106 and transducer assembly 108 from metallic bracket 100, encasement 106 may be slid off bracket 100 or oral appliance 18 may be removed entirely from user's tooth or teeth TH. FIG. 14B illustrates a perspective view of encasement 106 slidingly removed from metallic bracket 100.

Figure 15:
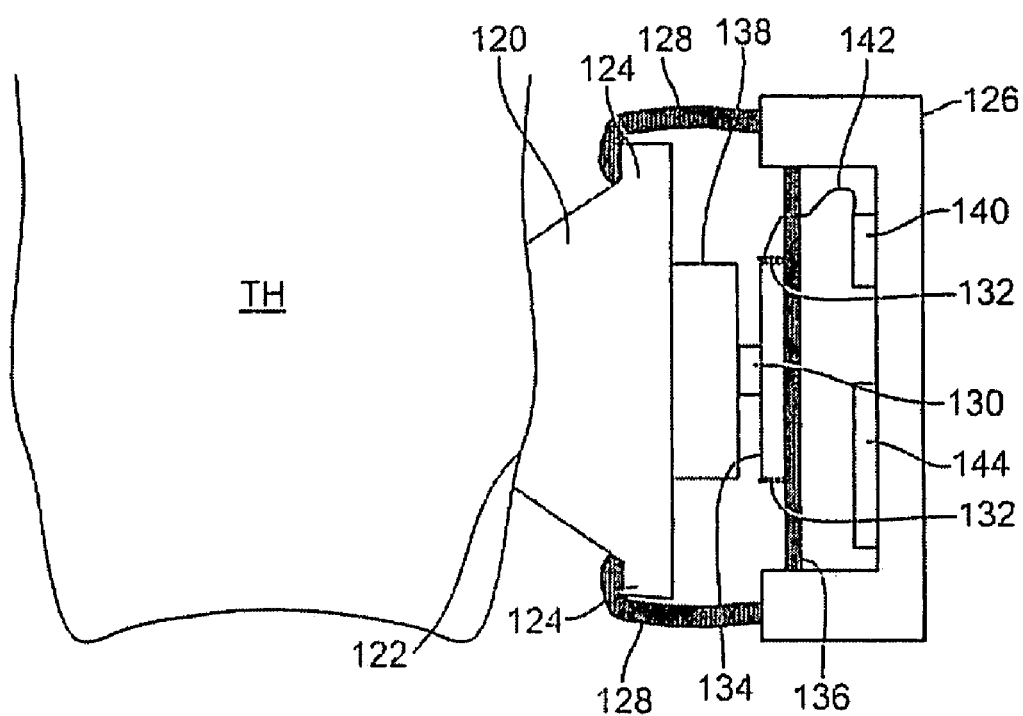
FIG. 15 illustrates a partial cross-sectional end view of another variation of a system utilizing a bracket mounted to the underlying tooth or teeth.

FIG. 15 illustrates a partial cross-sectional end view of another variation of a system utilizing a bracket 120 fabricated from any of the materials described above and mounted to the underlying tooth or teeth TH. This variation may utilize bracket 120 attached or otherwise affixed against mounting surface 122. Bracket 120 may define one or more mounting members or surfaces 124 upon which housing 126 may be secured via one or more securement members 128 extending from housing 126 to grasp or mechanically lock onto mounting members or surfaces 124. The one or more securement members 128 may be fabricated from a metallic or plastic member such as a clip or soft rubber boot.

Housing 126 not only provides mass for enhancing the vibrational transmission, but it also encapsulates the removable electronics and actuators, etc. An alignment member or feature 130 (e.g., a rod, dowel, or cylindrical projection which aligns the coil 132 with magnet 138) may be configured as a weak magnet poled in such a direction that its field interacts with the permanent magnet 138 to guide the motion of the transducer against bracket 120. In this variation, coil 132 may be wound about bobbin 134, which may be mounted against mounting substrate or surface 136 contained within housing 126. Coil 132 may interact with an adjacent permanent magnet 138 which vibrates against bracket 120. Moreover, coil 132 may be connected via electrical connector 142 leading to electronics 140. Power supply 144 may also be in electrical communication with the various elements contained within housing 126.

In yet another variation, FIG. 16A shows an end view of bracket 160 which may contain magnetic component 166, which may be ferromagnetic or electromagnetic, for removably coupling via magnetic attraction to housing 162 which may also contain a complementary magnetic component 168 for coupling to magnetic component 166. One or more alignment members or arms 164 defined along bracket 160 may facilitate the alignment of bracket 160 with housing 162 by aligning with alignment step 170. FIG. 16B shows another variation where bracket 160 may be configured such that the entire bracket is magnetic 172 for magnetically coupling to housing 162.

FIG. 16C shows yet another variation where a magnetic component 174 may be disposed at a first end of housing 162 and a complementary magnetic component 176 may be disposed at a first end of bracket 160. Having the magnetic components disposed along a single portion of bracket 160 and housing 162 may help to align housing 168 in a desired orientation when sliding housing 168 upon bracket 160.

Another variation is illustrated in the end and side views of FIGS. 17A and 17B, which show bracket 180 configured into a cylindrical configuration. Cylindrical bracket 180 may be adhered to attached to tooth TH via attachment 184 and is sufficiently sized to fit comfortably within the user's mouth. For instance, suitable dimensions for bracket 180 may range from 5 to 10 mm in diameter and 10 to 15 mm in length. Although illustrated in a cylindrical configuration, bracket 180 may be variously shaped, e.g., ovoid, cubicle, etc.

An electronics and/or transducer assembly 182 having an outer surface configured with screw threading 190 may be screwed into threaded housing opening 188 of bracket 180, as shown in the assembly side view of FIG. 17C. By rotating assembly 182 into bracket 180, e.g., by utilizing screw guide 186 as shown in FIG. 17D, a secure attachment and vibrational coupling may be achieved. Housing 180 may be removed from bracket 180 by reversing the direction of rotation of housing 180.

Figure 18A:
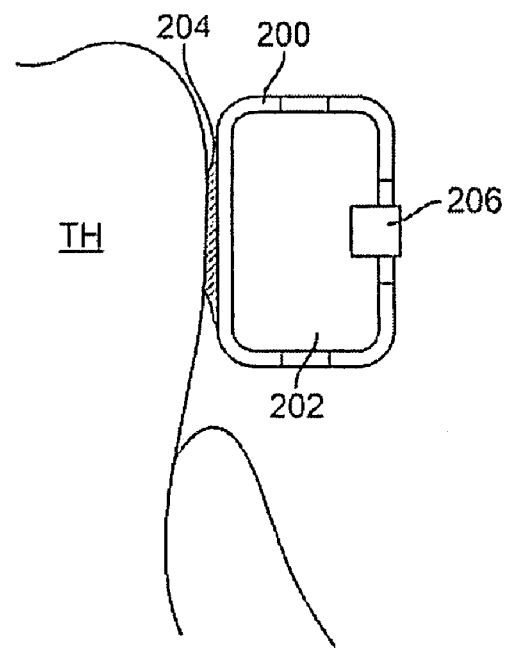
FIG. 18A shows an end view of another variation of a bracket which defines a receiving channel into which the electronics and/or transducer assembly may be positioned and secured via retaining tab.
Figure 18B:
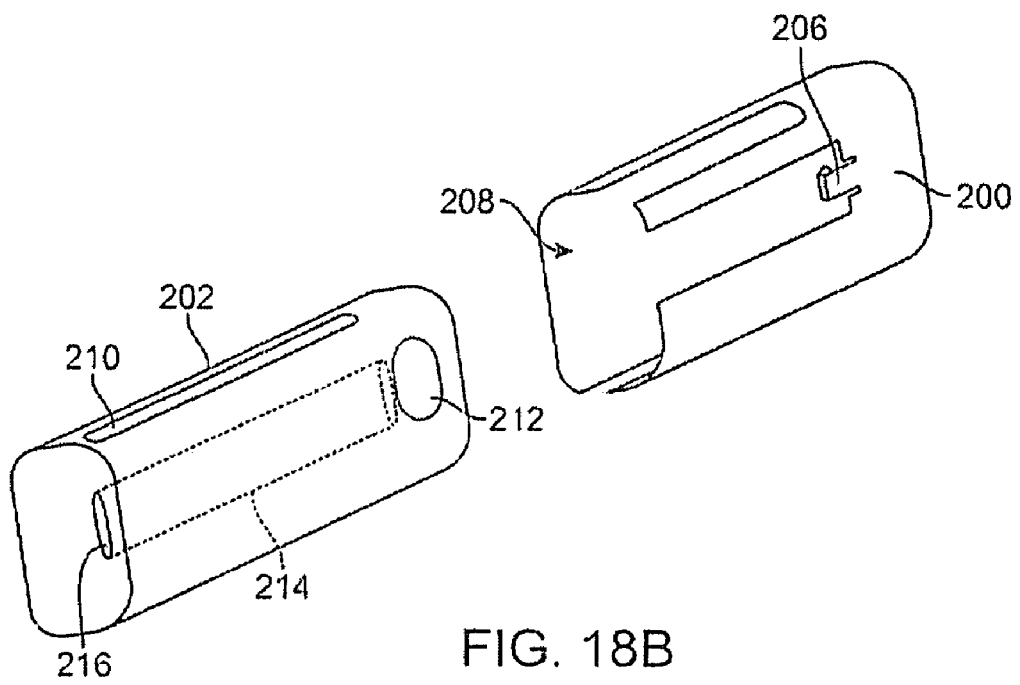
FIG. 18B shows a perspective view of the electronics and/or transducer assembly removed from the bracket.

FIG. 18A shows an end view of another variation utilizing bracket 200 attached to tooth TH via attachment 204 and which defines a receiving channel 208 into which electronics and/or transducer assembly 202 may be positioned and secured via retaining tab 206. As shown in FIG. 18B, a perspective view of the assembly with assembly 202 removed from bracket 200 illustrates the housing of assembly 202 defining one or more tool alignment grooves 210 along one or both sides of the housing. A tool opening 216 is defined along a proximal end of the housing and opens into a removal tool channel 214 defined through the length of assembly 202. Moreover, retaining tab receiving opening 212 is also defined near or at a distal end of the housing for receiving the retaining tab 206 when assembly 202 is inserted within bracket 200.

Figure 19A:
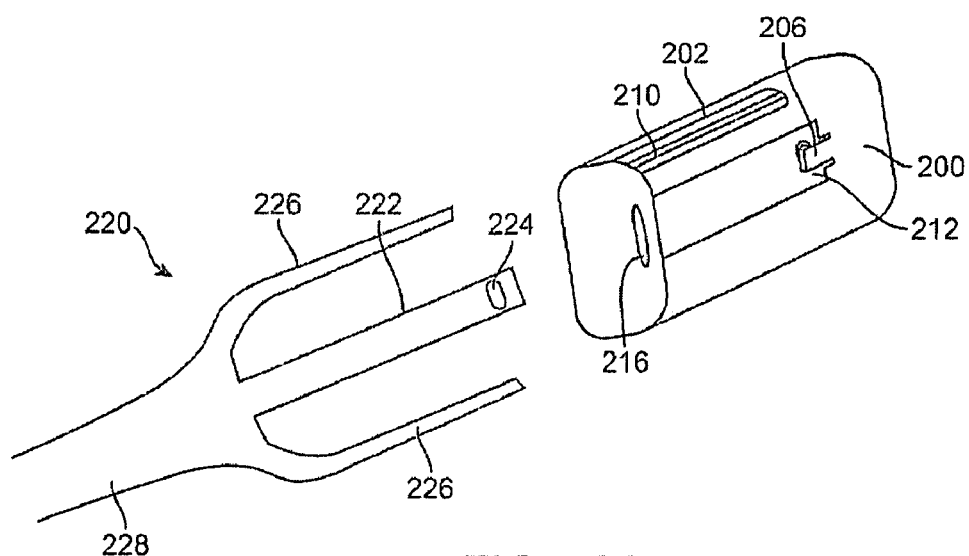
FIG. 19A shows a removal tool prior positioned to remove the electronics and/or transducer assembly from the bracket.

As shown in FIG. 19A, assembly 202 has been slid within bracket 200 and retaining tab 206 has been engaged within tab receiving opening 212. To remove assembly 202 from bracket 200, removal tool 220 may be used to release and remove assembly 202. Removal tool 220 may comprise central member 222 extending from elongate member 228. An engaging step 224 may be defined near or at a distal end of central member 222 for releasing tab 206 and two tool alignment members or prongs 226 may also extend from elongate member 228 in parallel on either side of central member 222.

Figure 19B:
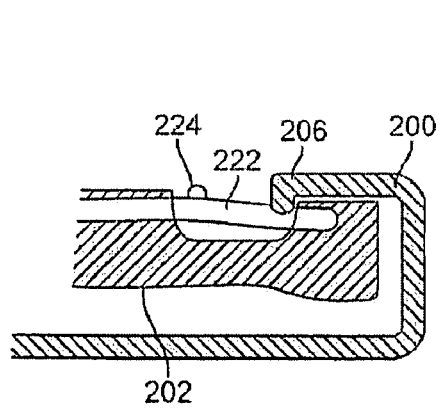
FIGS. 19B and 19C show partial side and top views, respectively, of an engaging step of the removal tool advanced to release the retaining tab from the electronics and/or transducer assembly.
Figure 19C:
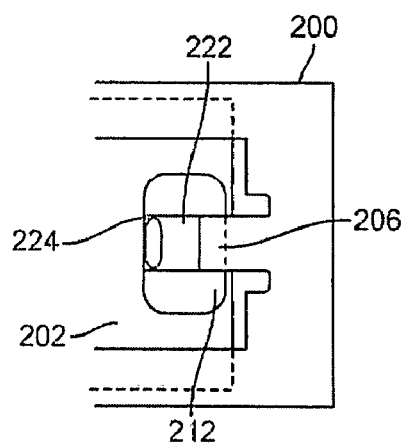

During removal, engaging step 224 and central member 222 may be inserted into opening 216. With alignment members 226 slid into their respective alignment grooves, defined along either side of assembly 202, engaging step 224 may be advanced until a distal portion of central member 222 releases tab 206 from tab receiving opening 212, as shown in the partial cross-sectional side view of FIG. 19B. With tab 206 disengaged, engaging step 224 may catch upon the edge of opening 212, as shown in FIG. 19B and the top view of FIG. 19C, allowing central member 222 and step 224 to pull assembly 202 from bracket 200 for removal.

Figure 20A:
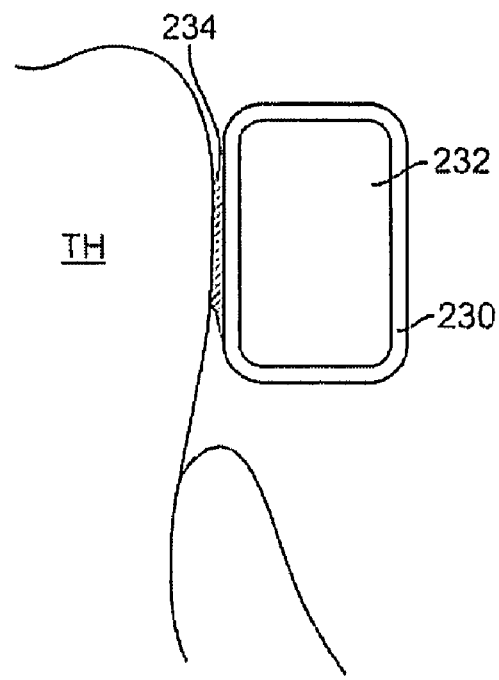
FIG. 20A shows an end view of another variation where of a bracket likewise attached to a tooth or teeth.
Figure 20B:
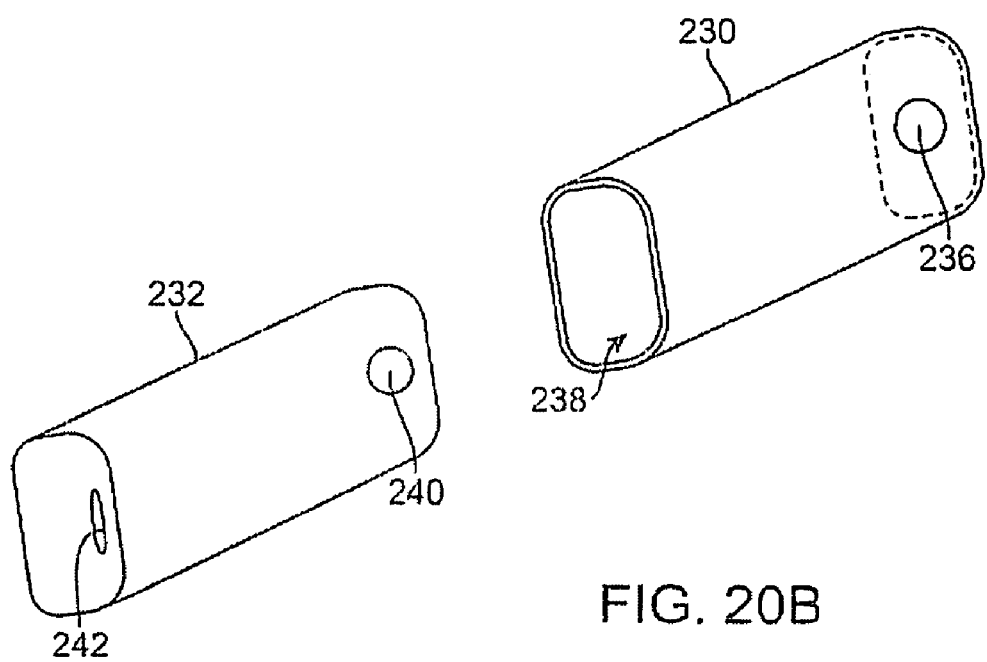
FIG. 20B shows a perspective view of the assembly removed from receiving channel of the bracket.

FIG. 20A shows an end view of another variation where bracket 230 may likewise be attached to tooth or teeth TH via attachment 234 and contain electronics and/or transducer assembly 232 within. Although illustrated as having an oval shape, any number of configurations may be utilized. FIG. 20B shows a perspective view of assembly 232 removed from receiving channel 238 of bracket 230. Assembly 232 may define a removal tool opening 242 at a proximal end and a protruding stop 240, e.g., ball, spring, etc., which may project at least partially from a surface of assembly 232. Bracket 230 may define a stop engagement opening 236 near or at a distal end of the bracket 230 such that when assembly 232 is initially inserted within bracket 230, stop 240 may be depressed into assembly 232 until released into stop engagement opening 236, thus functioning as a locking mechanism for retaining assembly 232 within bracket 230.

Figure 21A:
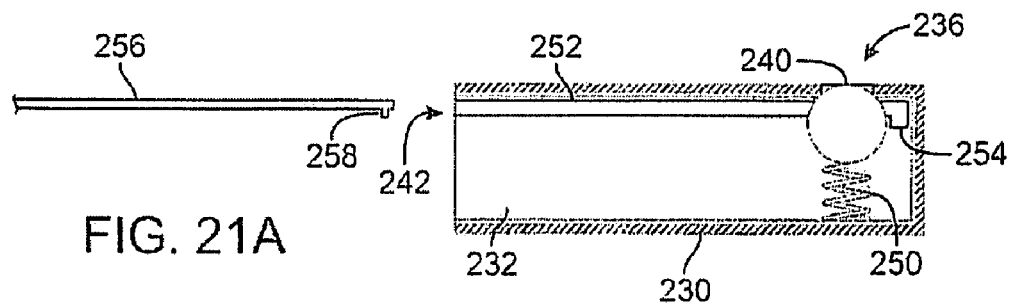
FIGS. 21A to 21D illustrate partial cross-sectional side views of one example for the detachment and removal of the electronics and/or transducer assembly from the bracket utilizing a removal tool.
Figure 21B:
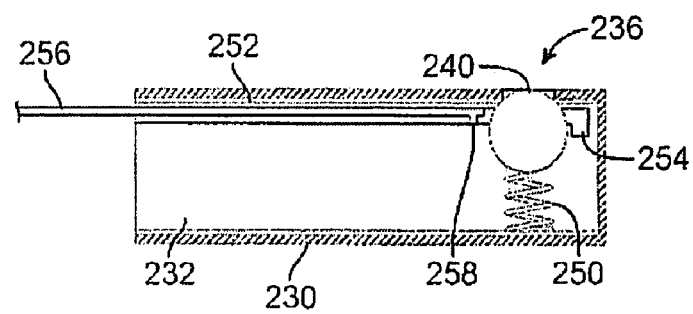
Figure 21C:
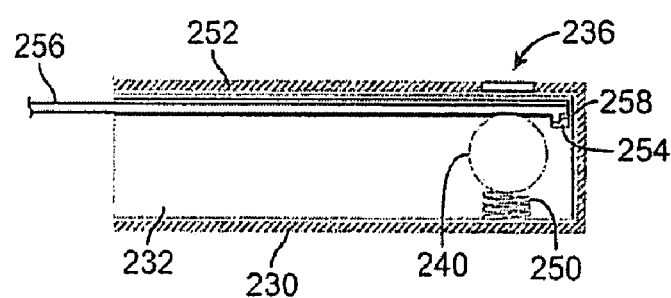
Figure 21D:
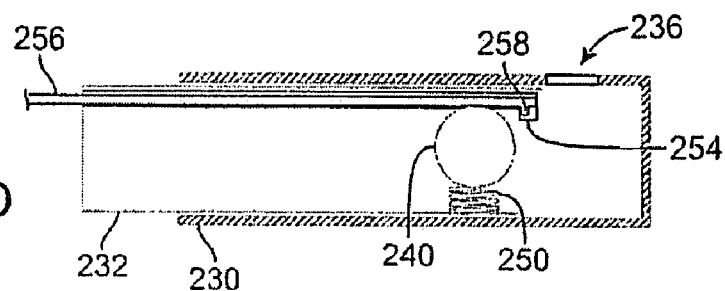

To remove assembly 232 from bracket 230, an elongate removal tool 256 having a step 258 defined near or at a distal end of tool 256 may be inserted into removal tool receiving channel 252 defined within assembly 242, as illustrated in FIG. 21A. Tool 256 may be advanced through channel 252 until it contacts stop 240, illustrated here as a spherical ball protruding through engagement opening 236 of bracket 230, as shown in FIG. 21B. Step 258 may be urged distally to push stop 240 out of engagement with opening 236 until tool 256 has been pushed over stop 240 to release assembly 232 from bracket 230. With stop 240 compressed against biasing element 250, e.g., a spring, tool 256 may be further advanced until step 258 engages engagement step 254, which is defined at the end of tool receiving channel 252, as shown in FIG. 21C. With tool 256 engaged via step 258 to engagement step 254, assembly 232 may then be slid proximally out from bracket 230 for removal, as shown in FIG. 21D.

Figure 22A:
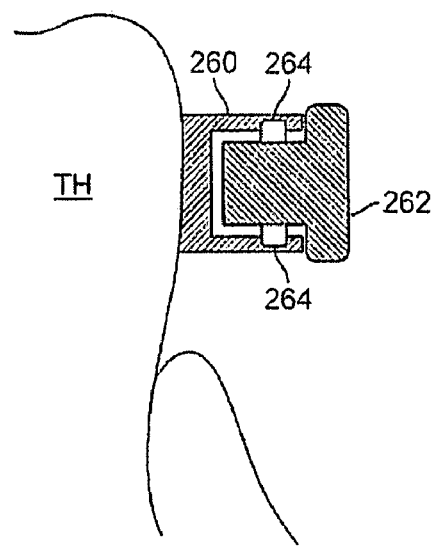
FIG. 22A shows an end view of another variation utilizing a bracket and a removable electronics and/or transducer assembly which may be coupled via a sliding mechanism and alignment members protruding from assembly.
Figure 22B:
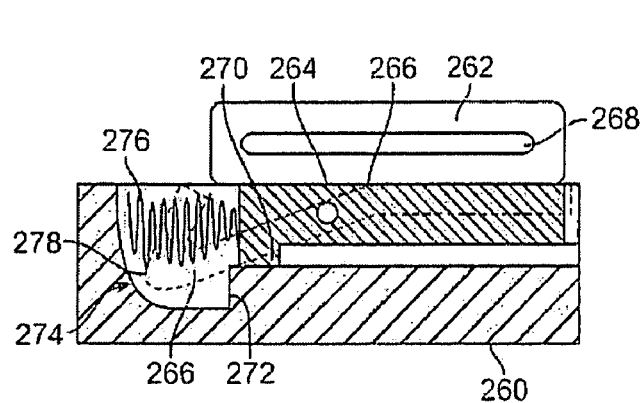
FIGS. 22B and 22C show partial cross-sectional side and end views, respectively, of an assembly positioned partially along the bracket prior to its secure engagement.
Figure 22C:
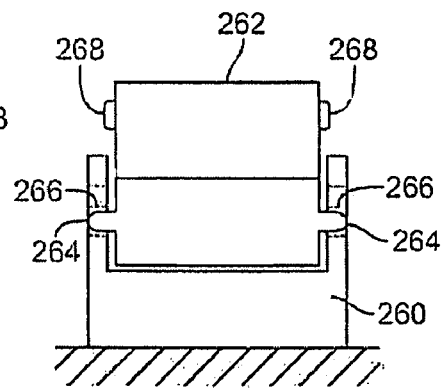

FIG. 22A shows an end view of another variation utilizing bracket 260 and removable electronics and/or transducer assembly 262 which may be coupled via a sliding mechanism and alignment members 264 protruding from assembly 262. FIGS. 22B and 22C show partial cross-sectional side and end views, respectively, of assembly 262 positioned partially along bracket 260 prior to secure engagement. Assembly 262 may define alignment members 264 protruding from either side of the housing and tool applicator rails 268, as described in further detail below, also protruding from either side of the housing along the length of assembly 262. A distal end of assembly 262 also defines a stop member 270 protruding from the housing for engagement with bracket 260. Bracket 260 defines one or more sliding tracks 266 along a length of bracket 260 through which the alignment members 264 may be inserted and guided through. Tracks 266 may further define a curved portion 278 along a distal end of sliding track 266, as described further below. A distal end of bracket 260 also defines a retaining step 272 for engagement with stop member 270 of assembly 262. A biasing element 276, e.g., a spring, may also be positioned within a cavity 274 defined near or at a distal portion of bracket 260.

Figure 23A:
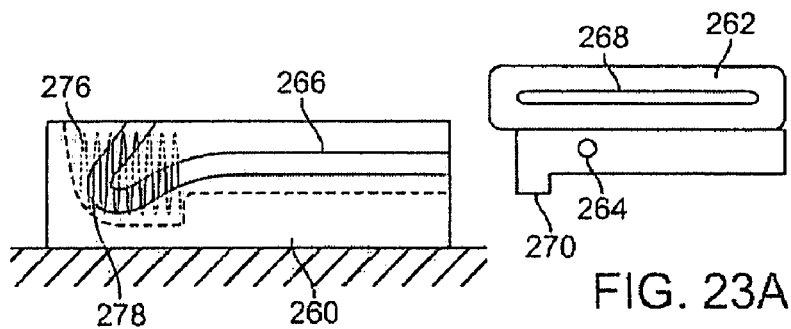
FIGS. 23A to 23D illustrate partial cross-sectional side views of an example for engaging and disengaging a removable electronics and/or transducer assembly from its bracket.
Figure 23B:
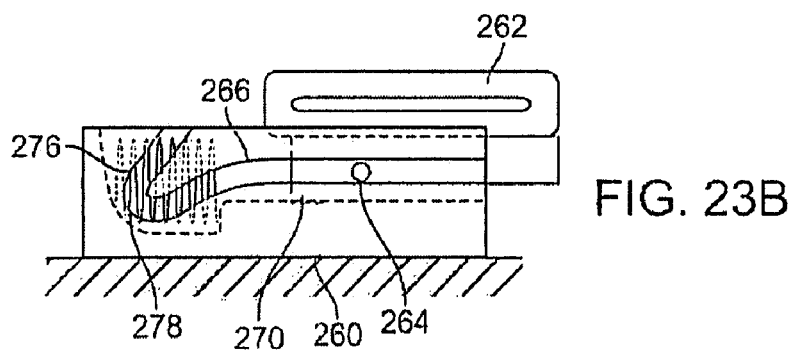
Figure 23C:
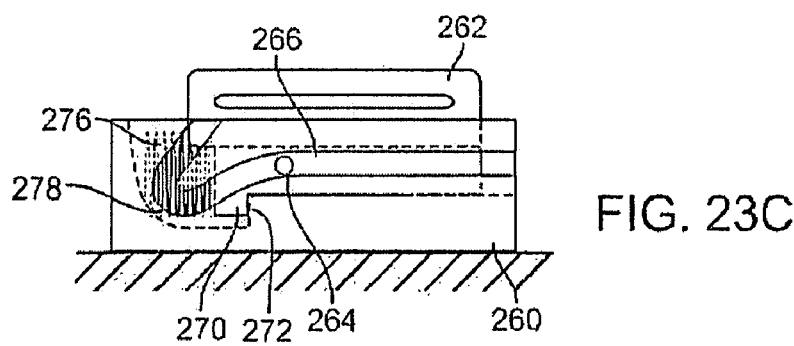
Figure 23D:
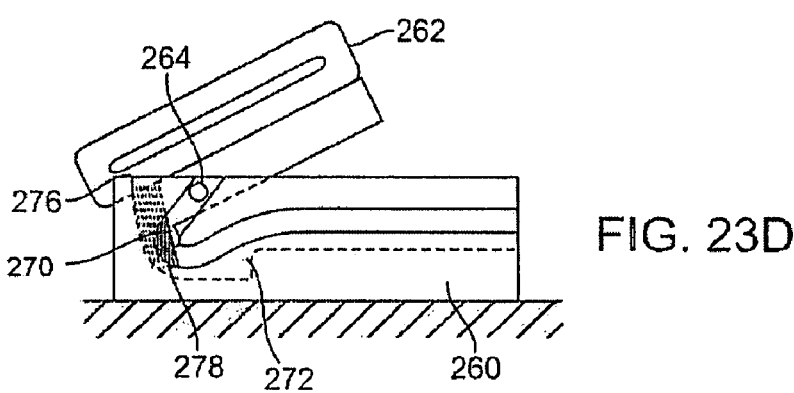

In use, when assembly 262 is to be coupled to bracket 260, alignment members 264 may be inserted into a proximal end of sliding track 266 and advanced therealong, as shown in FIGS. 23A and 23B. Assembly 262 may be urged distally until it contacts biasing element 276 contained within the distal portion of bracket 260 whereupon assembly 262 may be further urged distally while compressing biasing element 276. Sliding track 266 may be curved in such a manner where further advancement of assembly 262 forces stop member 270 to become engaged against retaining step 272. With the compressed biasing element 276 pushing against assembly 262, stop member 270 may be secured against retaining step 272 to inhibit or prevent the release of assembly 262, as shown in FIG. 23C. To release assembly 262 from bracket 260, assembly 262 may be pushed further distally relative to bracket 260 to further compress biasing element 276. With the distal portion 278 of sliding track 266 curved transversely relative to the proximal portion of track 266, alignment members 264 may be slid through the distal portion 278 and released from bracket 260 for removal, as shown in FIG. 23D.

Figure 24A:
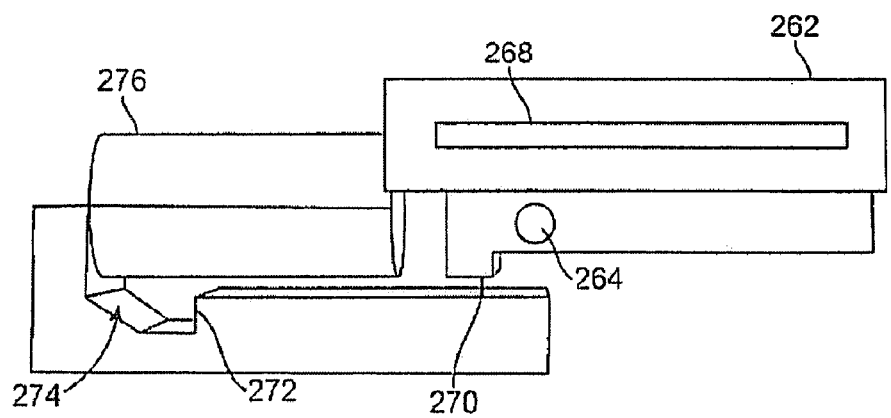
FIGS. 24A and 24B illustrate side views of the electronics and/or transducer assembly prior to engagement with a retaining step with the other features removed for clarity to further illustrate the securement mechanism.
Figure 24B:
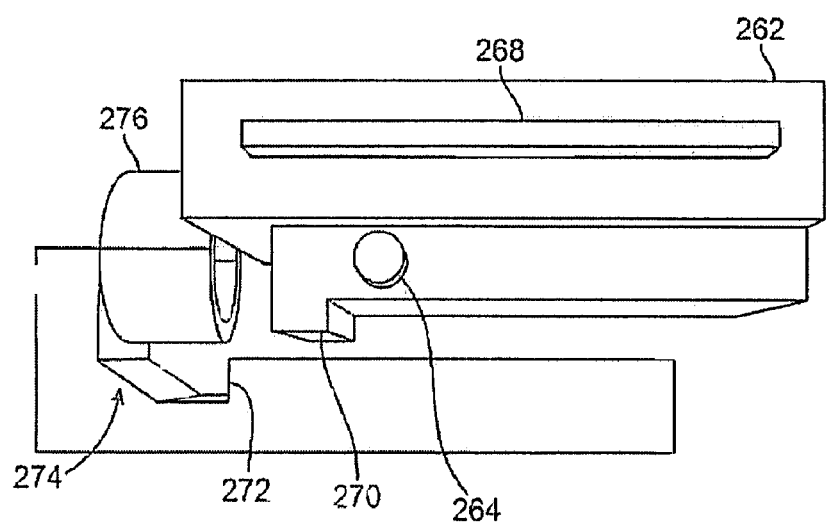

FIGS. 24A and 24B show side views of the assembly 262 prior to engagement with retaining step 272 with the other features removed for clarity to further illustrate the securement mechanism. As shown, as assembly 262 contacts and compresses biasing element 276, stop member 270 is eventually brought into engagement with retaining step 272 for securing assembly 262 to bracket 260.

Figure 25A:
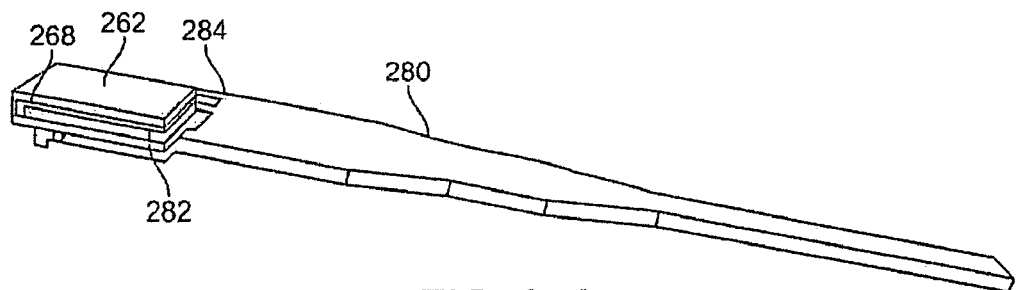
FIGS. 25A and 25B show perspective and detail perspective views, respectively, of the electronics and/or transducer assembly retained by an applicator tool for securement into the bracket.
Figure 25B:
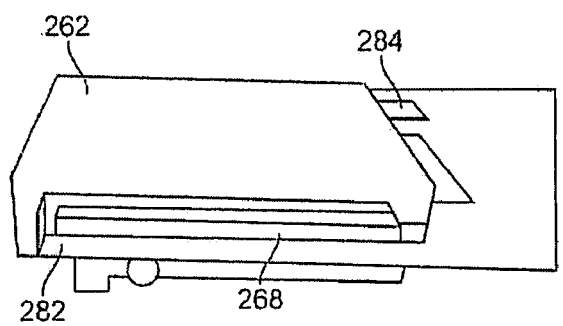
Figure 25D:
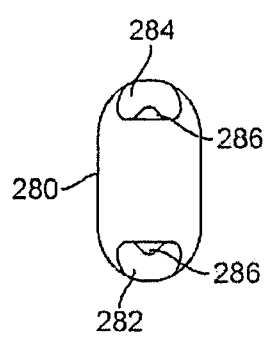
FIGS. 25C and 25D show top and end views, respectively, of the assembly and applicator tool illustrating the alignment channels defined along the lengths of the alignment members.
Figure 25C:
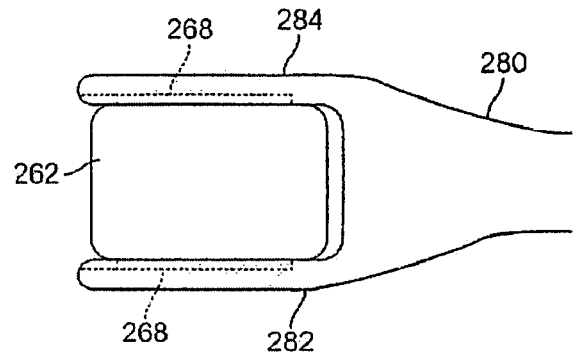

In order to facilitate the handling and introduction of assembly 262 into engagement with bracket 260, applicator tool 280 may be used, as shown in the perspective assembly view of FIG. 25A, to insert and secure assembly 262 relative to bracket 260. Tool 280 may define two alignment members 282, 284 which extend distally for releasably holding assembly 262 on either side. As seen in the detail perspective view of FIG. 25B, applicator rails 268 protruding from either or both sides of assembly 262 along the length of the housing may be slid into corresponding alignment channels 286 which are defined along the length of alignment members 282, 284 such that the applicator rails 268 are secured and transverse movement of assembly 262 relative to alignment members 282, 284 is inhibited or prevented, as shown in the top and end views of FIGS. 25C and 25D, respectively.

Figure 26A:
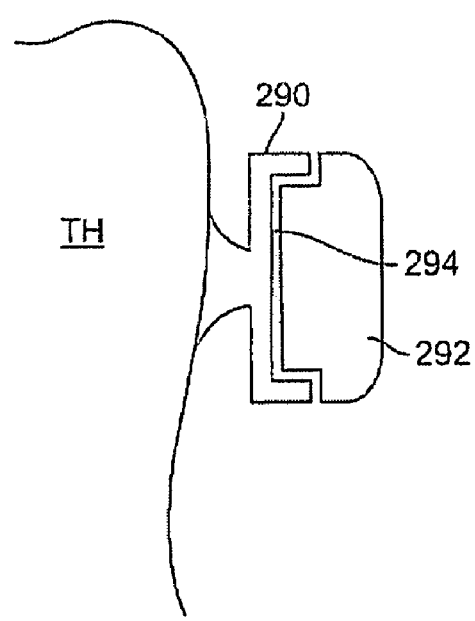
FIGS. 26A and 26B show end views of another coupling mechanism utilizing a chemical attachment.
Figure 26B:
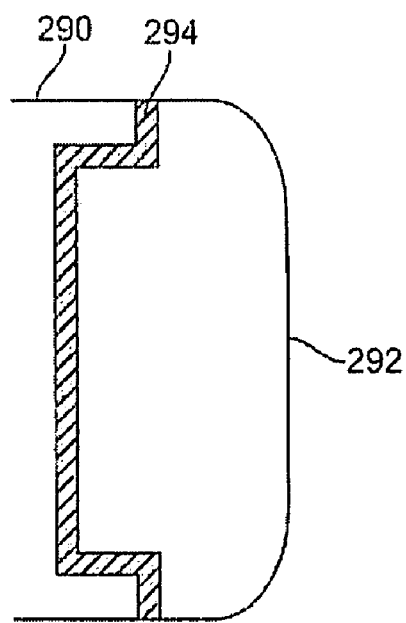

Aside from mechanical coupling mechanisms, chemical attachment may also be utilized. As shown in the end views of FIGS. 26A and 26B, electronics and/or transducer assembly 292 may be adhered to bracket 290 via a non-permanent adhesive 294. Examples of such temporary adhesive 294 may include, e.g., eugenol and non-eugenol cements. Examples of eugenol temporary cements include, but are not limited to, zinc oxide eugenol commercially available from Temrex (Freeport, N.Y.) or TempoCem® available from Zenith Dental (Englewood, N.J.). Other examples of non-eugenol temporary cements include, but are not limited to, cements which are commercially available such as PROVISCELL™ (Septodont, Inc., Ontario, Canada) as well as NOMIX™ (Centrix, Inc., Shelton, Conn.).

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 27A illustrates one example where multiple transducer assemblies 300, 302, 304, 306 may be placed on multiple teeth. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within non-overlapping frequency ranges between each assembly. As mentioned above, each transducer 300, 302, 304, 306 can be programmed or preset for a different frequency response such that each transducer may be optimized for a different frequency response and/or transmission to deliver a relatively high-fidelity sound to the user.

Moreover, each of the different transducers 300, 302, 304, 306 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user. For instance, a first transducer located, e.g., on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

Figure 27B:
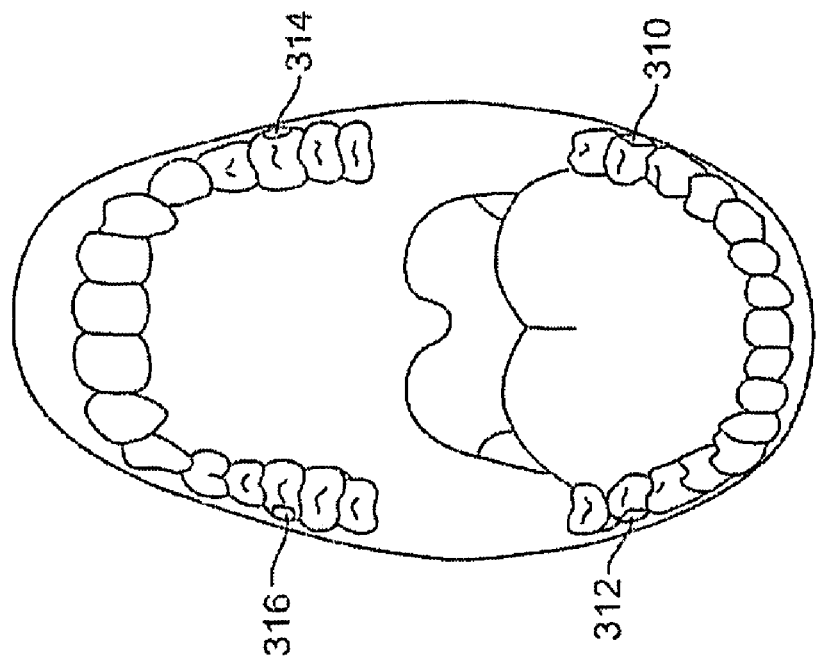
FIG. 27B illustrates another variation where at least one microphone (or optionally any number of additional microphones) may be positioned within the mouth of the user while physically separated from the electronics and/or transducer assembly.
Figure 27A:
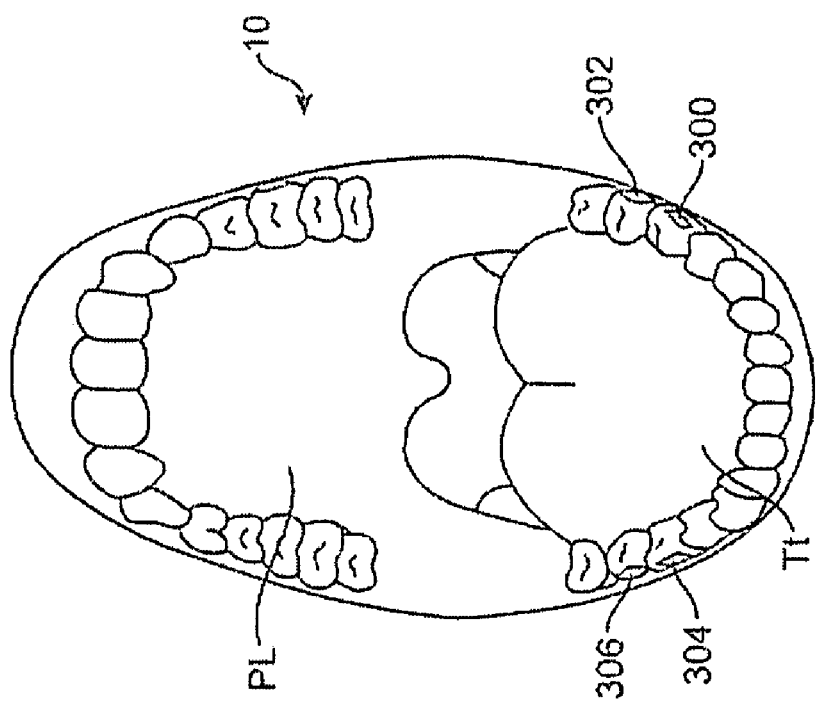
FIG. 27A illustrates an example where multiple transducer assemblies may be placed on multiple teeth.

In yet another variation for separating the microphone from the transducer assembly, FIG. 27B illustrates another variation where at least one microphone 312 (or optionally any number of additional microphones 314, 316) may be positioned within the mouth of the user while physically separated from the electronics and/or transducer assembly 310. In this manner, the one or optionally more microphones 312, 314, 316 may be wirelessly coupled to the electronics and/or transducer assembly 310 in a manner which attenuates or eliminates feedback from the transducer.

Further examples of these algorithms are shown and described in detail in U.S. patent application Ser. Nos. 11/672,239; 11/672,250; 11/672,264; and 11/672,271 all filed Feb. 7, 2007 and each of which is incorporated herein by reference in its entirety.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. An apparatus for transmitting vibrations via at least one tooth to facilitate hearing in a patient, comprising:
   a bracket affixed to a surface of the at least one tooth; and
   a housing assembly configured to engage more than one side of the at least one tooth without requiring anatomical modification of the at least one tooth,
   wherein the housing assembly is removably coupled to the bracket such that an actuatable transducer is placed in vibratory communication with the bracket and wherein the transducer conducts vibrations directly into the surface via the bracket.

2. The apparatus of claim 1 wherein the bracket is affixed to the surface via an adhesive or cement.

3. The apparatus of claim 2 wherein the adhesive or cement is selected from the group consisting of zinc oxide eugenol, zinc phosphate, zinc silico-phosphate, zinc polyacrylate, zinc-polycarboxylate, glass ionomer, resin-based, and silicate-based cements.

4. The apparatus of claim 1 wherein the bracket defines one or more projections configured to securely mate with the housing assembly so as to inhibit or prevent disconnection of the housing assembly when coupled to one another.

5. The apparatus of claim 1 wherein the bracket comprises a rail upon which the housing assembly slides.

6. The apparatus of claim 1 wherein the bracket assembly is integrated with an oral appliance which is configured to be placed upon and conform to the at least one tooth.

7. The apparatus of claim 1 wherein the bracket comprises a magnetic portion which is configured to couple to a complementary magnetic portion contained within the housing assembly.

8. The apparatus of claim 1 wherein the bracket comprises a cylindrical housing configured to receive the housing assembly having a threaded outer surface.

9. The apparatus of claim 1 wherein the bracket comprises a releasable retaining tab configured to engage an opening along the housing assembly.

10. The apparatus of claim 1 wherein the bracket defines an opening configured to receive a protruding stop projecting from the housing assembly.

11. The apparatus of claim 1 wherein the bracket comprises a biasing element configured to urge the housing assembly into a secure engagement via a retaining step.

12. The apparatus of claim 1 wherein the bracket and housing assembly are coupled via a temporary adhesive or cement.

13. The apparatus of claim 1 wherein the housing assembly comprises a processor in communication with the actuatable transducer.

14. The apparatus of claim 13 further comprising a battery contained within the housing assembly.

15. The apparatus of claim 1 wherein the housing assembly comprises an alignment member configured to align the housing relative to the bracket.

16. The apparatus of claim 1 further comprising an alignment tool having at least two members projecting distally, wherein the two members each define an alignment channel for slidingly receiving the housing assembly.

17. The apparatus of claim 1 further comprising at least one additional actuatable transducer in vibratory communication with the surface.

18. The apparatus of claim 17 wherein the at least one additional actuatable transducer is disposed within or upon at least one additional bracket affixed to a surface of an additional tooth.

19. The apparatus of claim 17 wherein each transducer is configured to provide a sound or vibrational queue indicative of a direction in which sound is detected relative to an orientation of a user.

20. A method of transmitting vibrations via at least one tooth, comprising:
   affixing a bracket onto a surface of the at least one tooth;
   coupling a removable housing assembly onto the bracket, wherein the housing assembly is configured to engage more than one side of the at least one tooth without requiring anatomical modification of the at least one tooth; and
   actuating a transducer within the housing assembly which is in vibratory communication with the bracket such that the transducer conducts vibrations directly into the surface via the bracket.

21. The method of claim 20 wherein affixing comprises adhering the bracket onto the surface via an adhesive or cement.

22. The method of claim 21 wherein adhering comprises permanently adhering the bracket onto the surface.

23. The method of claim 20 wherein coupling comprises magnetically coupling the housing assembly onto the bracket.

24. The method of claim 20 wherein coupling comprises sliding the housing assembly upon a rail defined along the bracket.

25. The method of claim 20 wherein coupling comprises screwing the housing assembly into a threaded receiving channel of the bracket.

26. The method of claim 20 wherein coupling further comprises securing the housing assembly to the bracket via a locking tab.

27. The method of claim 20 wherein coupling further comprises securing the housing assembly to the bracket via a stop member protruding from the housing assembly into the bracket.

28. The method of claim 20 wherein coupling further comprises securing the housing assembly to the bracket via a biasing element compressing a retaining step between the housing assembly and the bracket.

29. The method of claim 20 wherein coupling comprises positioning the housing assembly onto the bracket via an alignment tool.

30. The method of claim 20 wherein coupling comprises adhering the housing assembly to the bracket via a temporary adhesive or cement.

31. The method of claim 20 further comprising receiving an electronic signal representative of a received audio signal prior to actuating a transducer.

32. The method of claim 31 wherein receiving further comprises processing the electronic signal via a processor.

33. The method of claim 20 wherein actuating comprises actuating the transducer to correspond to a perceived audio signal.

34. The method of claim 20 further comprising actuating at least one additional transducer in vibratory communication with at least one additional bracket affixed upon an additional tooth.

35. The method of claim 20 further comprising removing the housing assembly from the bracket.

* * * * *